US012761150B2

(12) United States Patent
Lehtonen et al.

(10) Patent No.: US 12,761,150 B2
(45) Date of Patent: Oct. 13, 2026

(54) APPARATUS AND METHOD FOR DETECTING FLUORESCENCE

(71) Applicant: MARGINUM OY, Tampere (FI)

(72) Inventors: Samu Juhani Rafael Lehtonen, Tampere (FI); Antti-Pekka Elomaa, Tampere (FI); Juho Hermanni Leskinen, Tampere (FI); Dmitry Vladimirovich Semenov, Tampere (FI)

(73) Assignee: MARGINUM OY, Tampere (FI)

( * ) Notice: Subject to any disclaimer, the term of this patent is extended or adjusted under 35 U.S.C. 154(b) by 551 days.

(21) Appl. No.: 18/263,238

(22) PCT Filed: Jan. 28, 2022

(86) PCT No.: PCT/FI2022/050055
§ 371 (c)(1),
(2) Date: Jul. 27, 2023

(87) PCT Pub. No.: WO2022/162277
PCT Pub. Date: Aug. 4, 2022

(65) Prior Publication Data

US 2024/0110869 A1 Apr. 4, 2024

(30) Foreign Application Priority Data

Jan. 29, 2021 (FI) ..................................... 20215096

(51) Int. Cl.
*G01N 21/64* (2006.01)
*G01N 33/53* (2006.01)
*G01N 33/543* (2006.01)

(52) U.S. Cl.
CPC ..... *G01N 21/6428* (2013.01); *G01N 33/5308* (2013.01); *G01N 33/54386* (2013.01); *G01N 2021/6439* (2013.01)

(58) Field of Classification Search
CPC ... G01N 2021/6439; G01N 2021/6441; G01N 2021/6482; G01N 21/6408;
(Continued)

(56) References Cited

U.S. PATENT DOCUMENTS

2005/0064582 A1* 3/2005 Wittwer ................ B01L 3/5082
435/288.1
2008/0085550 A1* 4/2008 Werner .............. G01N 21/4795
356/319

(Continued)

FOREIGN PATENT DOCUMENTS

EP 1359420 B1 4/2010
JP H0816873 A 1/1996

(Continued)

OTHER PUBLICATIONS

Ann Johansson et al., "5-Aminolevulinic Acid-induced Protoporphyrin IX Levels in Tissue of Human Malignant Brain Tumors," Photochemistry and Photobiology; Aug. 6, 2010; pp. 1373-1378.

(Continued)

*Primary Examiner* — Jennifer Wecker
(74) *Attorney, Agent, or Firm* — NIXON & VANDERHYE

(57) ABSTRACT

Disclosed is an apparatus (100) for detecting fluorescence of a sample (118, 119) obtained from an object, the sample (118, 119) comprising one or more fluorophores and representing a disease or condition, and the sample (118, 119) being transported away from the object in a transparent conduit (131). The apparatus comprises a housing (101) comprising one or more light sources (110) and one or more light receivers (120), and a computing device (180). It is also disclosed a method for detecting fluorescence of a sample (118, 119) obtained from an object, the sample (118, 119) comprising one or more fluorophores and representing a disease or condition, and the sample (118, 119) being (Continued)

transported away from the object in a transparent conduit (131). Furthermore, it is disclosed uses of the apparatus (100) and a kit-of-parts comprising the apparatus (100).

16 Claims, 6 Drawing Sheets

(58) Field of Classification Search
CPC .. G01N 21/6428; G01N 21/645; G01N 21/85; G01N 33/5308; G01N 33/54386
See application file for complete search history.

(56) References Cited

U.S. PATENT DOCUMENTS

| | | | | |
|---|---|---|---|---|
| 2008/0268469 | A1* | 10/2008 | Srienc | G01N 15/1433 435/287.1 |
| 2009/0112482 | A1* | 4/2009 | Sandstrom | G01N 21/6452 702/19 |
| 2011/0249109 | A1* | 10/2011 | Fine | G01N 21/6458 348/79 |
| 2014/0358447 | A1 | 12/2014 | Doyle et al. | |
| 2015/0374308 | A1 | 12/2015 | Tichauer et al. | |
| 2017/0370845 | A1 | 12/2017 | Ito et al. | |
| 2018/0128676 | A1* | 5/2018 | Katzlinger | G01J 1/0238 |
| 2018/0256065 | A1 | 9/2018 | Ji et al. | |
| 2018/0259762 | A1* | 9/2018 | Fujimoto | G01N 21/6428 |
| 2019/0384048 | A1 | 12/2019 | Valdes et al. | |
| 2020/0026090 | A1* | 1/2020 | Hargis | G02B 27/0961 |
| 2020/0204776 | A1 | 6/2020 | Themelis | |

FOREIGN PATENT DOCUMENTS

| | | |
|---|---|---|
| JP | H1123114 A | 1/1999 |
| JP | H1123224 A | 1/1999 |
| JP | 4-076859 | 2/2008 |
| JP | 2011-185841 | 9/2011 |
| JP | 2014-153199 | 8/2014 |
| KR | 20180000304 A | 1/2018 |
| WO | 2018/131096 | 7/2018 |
| WO | 2020/221485 | 11/2020 |

OTHER PUBLICATIONS

Taniguchi et al., Improving Convenience and Reliability of 5-ALAInduced Fluorescent Imaging for Brain Tumor Surgery, Springer International Publishing, Nov. 18, 2015, pp. 209-217.
International Search Report for PCT/FI2022/050055 mailed Apr. 5, 2022, 3 pages.
Search Report for FI20215096 dated Sep. 9, 2021, 5 pages.
International Preliminary Report on Patentability for PCT/FI2022/050055, mailed Mar. 23, 2023, 30 pages.
Office Action, issued in Korean Patent Application No. 10-2023-7029262 dated Sep. 25, 2025.
Jul. 9, 2024 Office Action issued in Japanese Patent Application No. 2023-546030, pp. 1-3 [machine translation included].
Office Action, issued in Indonesian Patent Application No. P00202307945 dated Aug. 1, 2025.
Office Action, issued in Chinese Patent Application No. 202280015954.2 dated Apr. 17, 2026.

* cited by examiner

APPARATUS AND METHOD FOR DETECTING FLUORESCENCE

This application is the U.S. national phase of International Application No. PCT/FI2022/050055 filed Jan. 28, 2022, which designated the U.S. and claims priority to FI patent application No. 20215096 filed Jan. 29, 2021, the entire contents of each of which are hereby incorporated by reference.

TECHNICAL FIELD

The present disclosure relates generally to detecting fluorescence of a sample. More specifically, the present disclosure relates to an apparatus for detecting fluorescence of a sample comprising one or more fluorophores; and to methods for detecting fluorescence of a sample comprising one or more fluorophores.

BACKGROUND

Fluorescence inducing photodynamic substances, such as 5-aminolevulinic acid (5-ALA), are increasingly used in surgical procedures for tumors such as grade 3-4 gliomas. Fluorescent markers and fluorophores, when excited at a certain wavelength, generate characteristic fluorescence that, for example, assist a surgeon in defining the infiltration zone between tumor cells and healthy tissue. With current methods, the detection is based on the fluorescence seen by the surgeon's eyes and the average tumor removal rate is 80%. It has been shown that the best benefits are associated for patients with at least 98% tumor removed and no functionally important brain tissue damaged. The tumor is mechanically removed using various techniques, predominantly by removal of the tissues with an ultrasonic aspirator or surgical suction device after manual detachment of the tumor. Using the currently available surgical removal techniques, the resection rate is not sufficient, and the assessment of the healthy tissue border is unreliable.

Neurosurgeons utilize the drug 5-ALA, being e.g. 5-ALA or a salt, e.g. the hydrochloride salt, thereof, in fluorescence guided surgeries (FGS) of certain glioma-type brain tumors. Before the surgery, the patients are orally administered with the 5-ALA drug. 5-ALA is a compound in the porphyrin synthesis pathway; it is converted in human to protoporphyrin IX (PpIX), a fluorescent substance (a fluorophore), and further to heme by ferrochelatase. Therefore, 5-ALA may also be considered a prodrug of PpIX. Cancer cells lack or have reduced ferrochelatase activity and this, among other potential reasons, results in accumulation of PpIX in cancer cells. During FGS, the surgical cavity is exposed to PpIX exciting blue light, generating fluorescence at a peak wavelength of ca. 635 nm, generated by PpIX, of the cancer cells of the tumor that helps to delineate the tumor for its removal. The fluorescence of PpIX (at a peak wavelength of ca. 635 nm) is not visible in white light, but under blue excitation light the tumor comprising PpIX stands out compared to other. Therefore, in FGS, to see fluorescence, surgeons change the light, which the microscope emits, from white to blue. However, when the surgical cavity is exposed to PpIX exciting blue light, the contrast between other tissues (excluding tumor) is significantly reduced. Thus, during the time the cavity is emitted with blue light, it is difficult for the surgeon to distinguish vital or important tissue not to be removed. Therefore, while tumor removal occurs mainly using white light, its identification is performed using blue excitation light.

Fluorescence detection is thus limited to the surgeon's vision. The contemporary FGS techniques predominantly depend on subjective assessment of perceivable fluorescent traces, which is believed to lead to susceptibility for both type 1 and type 2 errors. In parallel to the required manual configurations of the light sources, the utilization of contemporary FGS slows down operative performance. Furthermore, during the tumor removal, the visual performance is limited by, among other things, the limited field of view of the surgical microscope and the invisible remains and angles. Due to technical limitations, removal strategies depend on the recollection of observed fluorescence deposits and, in some cases, on optically filtered video recording. Also, the human visual system lack sensitivity to detect clinically relevant concentrations of fluorophores, e.g. PpIX, and the visual specificity is limited. Exposing samples comprising fluorophores to excitation light causes fluorescence to fade over time due to photobleaching, which is dependent on both the excitation time and intensity of the excitation light. Photobleaching is caused e.g. by reactions between the fluorophore and surrounding molecules, thus limiting the use of fluorophores.

Several other experimental optical imaging techniques such as Raman spectroscopy, optical coherence tomography (OCT) and diffuse reflectance spectroscopy (DRS) have been developed in search of neurosurgical indications. Most of the described optical imaging methods have been described to be suitable for neurosurgical tumor demarcation and functional measuring in the present scientific literature, however, their contemporary intraoperative applications predominantly require separate, bulky sensors and intricate visualization methods that impair the surgeon's proficiency.

Therefore, in light of the foregoing discussion, there exists a need to overcome the aforementioned drawbacks associated with detecting fluorescence of a sample comprising one or more fluorophores and representing a disease or condition.

BRIEF DESCRIPTION

According to an aspect, there is provided the subject matter of the independent claims. Embodiments are defined in the dependent claims. The scope of protection sought for various embodiments of the invention is set out by the independent claims. The embodiments, examples and features, if any, described in this specification that do not fall under the scope of the independent claims are to be interpreted as examples useful for understanding various embodiments of the invention.

The present disclosure seeks to provide an apparatus for detecting fluorescence of a sample obtained from an object, the sample comprising one or more fluorophores and representing a disease or condition, and the sample being transported away from the object in a transparent conduit. The present disclosure also seeks to provide a method for detecting fluorescence of a sample method for detecting fluorescence of a sample obtained from an object, the sample comprising one or more fluorophores and representing a disease or condition, and the sample being transported away from the object in a transparent conduit. The present disclosure seeks to provide a solution to the existing problems of detecting fluorescence of a sample comprising one or more fluorophores, especially of detecting fluorescence of a sample comprising one or more fluorophores during fluorescence guided surgery. An aim of the present disclosure is to provide a solution that overcomes and improves at least partially the problems encountered in prior art.

In one aspect, an embodiment of the present disclosure provides an apparatus for detecting fluorescence of a sample obtained from an object, the sample comprising one or more fluorophores and representing a disease or condition, and the sample being transported away from the object in a transparent conduit, the apparatus comprising:

- a housing being adapted to surround at least a part of the transparent conduit, the housing comprising:
  - one or more light sources operable to emit light towards the sample being transported in the transparent conduit, and
  - one or more light receivers operable to detect fluorescence generated by one or more fluorophores comprised in the sample being transported in the transparent conduit,
- a computing device, the computing device comprising computing means for:
  - receiving a first signal from at least one of the one or more light receivers, the first signal being proportional to the detected fluorescence by the at least one of the one or more light receivers;
  - comparing the first signal to a predefined threshold for the first signal; and
  - outputting a first information indicating comparison result.

In another aspect, an embodiment of the present disclosure provides a method for detecting fluorescence of a sample obtained from an object, the sample comprising one or more fluorophores and representing a disease or condition, and the sample being transported away from the object in a transparent conduit, the method comprising:

- i) transporting a sample, comprising one or more fluorophores and representing a disease or condition, in a transparent conduit away from the object;
- ii) emitting light towards the sample being transported in the conduit;
- iii) detecting fluorescence generated by one or more fluorophores comprised in the sample being transported in the conduit; iv) generating a first signal being proportional to the detected fluorescence;
- v) comparing the first signal to a predefined threshold for the first signal; and
- vi) outputting a first information indicating comparison result.

In another aspect, an embodiment of the present disclosure provides a use of an apparatus as disclosed in the present disclosure in a method selected from the group consisting of an invasive medical treatment method, a detection method of a diseased tissue or a diseased body fluid comprising one or more fluorophores and representing a disease or condition, a detection method of a tumor and in the diagnosis of cancer. Preferably, the diagnosis of cancer is in vitro or ex vivo diagnosis of cancer.

In another aspect, an embodiment of the present disclosure provides a kit-of-parts of an apparatus as disclosed in the present disclosure combined with a transparent conduit.

In another aspect, an embodiment of the present disclosure provides a method of surgery, a method of treatment of a disease or a condition, or an in vivo diagnosis of a disease or a condition using an apparatus as disclosed in the present disclosure.

In another aspect, an embodiment of the present disclosure provides a method for detecting fluorescence of a sample comprising one or more fluorophores and representing a disease or condition, using an apparatus as disclosed in the present disclosure.

In another aspect, an embodiment of the present disclosure provides an apparatus as disclosed in the present disclosure for carrying out a method as disclosed in the present disclosure.

Embodiments of the present disclosure substantially eliminate or at least partially address the aforementioned problems in the prior art of conventional apparatus and methods of fluorescence detection and embodiments of the present disclosure enable detecting visually invisible (to the human eye) low concentration traces of fluorescence.

Additional aspects, advantages, features and objects of the present disclosure would be made apparent from the drawings and the detailed description of the illustrative embodiments construed in conjunction with the appended claims that follow.

It will be appreciated that features of the present disclosure are susceptible to being combined in various combinations without departing from the scope of the present disclosure as defined by the appended claims.

BRIEF DESCRIPTION OF THE DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the present disclosure is not limited to specific methods and apparatuses disclosed herein. Moreover, those skilled in the art will understand that the drawings are not to scale, if not indicated otherwise. Wherever possible, like elements have been indicated by identical numbers.

Embodiments of the present disclosure will now be described, by way of example only, with reference to the attached drawings, in which.

Figure 1:
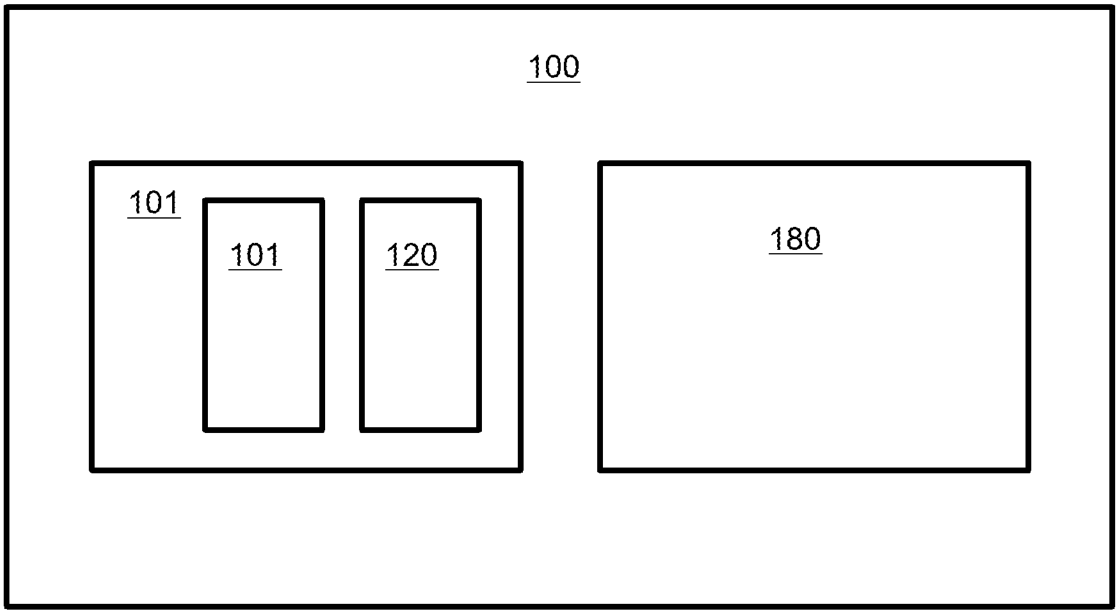
FIG. 1 is a block diagram of an apparatus, in accordance with an embodiment of the present disclosure.

In the accompanying drawings, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

DETAILED DESCRIPTION OF SOME EMBODIMENTS

The following detailed description illustrates embodiments of the present disclosure and ways in which they can be implemented. Although some modes of carrying out the present disclosure have been disclosed, those skilled in the art would recognize that other embodiments for carrying out or practising the present disclosure are also possible.

In one aspect, an embodiment of the present disclosure provides an apparatus for detecting fluorescence of a sample obtained from an object, the sample comprising one or more fluorophores and representing a disease or condition, and the sample being transported away from the object in a transparent conduit, the apparatus comprising:

a housing being adapted to surround at least a part of the transparent conduit, the housing comprising:
- one or more light sources operable to emit light towards the sample being transported in the transparent conduit, and
- one or more light receivers operable to detect fluorescence generated by one or more fluorophores comprised in the sample being transported in the transparent conduit, a computing device, the computing device comprising computing means for:
- receiving a first signal from at least one of the one or more light receivers, the first signal being proportional to the detected fluorescence by the at least one of the one or more light receivers;
- comparing the first signal to a predefined threshold for the first signal; and
- outputting a first information indicating comparison result.

Therefore, an apparatus of the present disclosure enables detection of fluorescence of a sample obtained from an object and being transported away from the object, particularly enabling near-real time detection of the sample. The terms "near-real time detection" as used herein and hereafter refers to the time between obtaining the sample from the object and the outputting of the first information indicating comparison result of the comparison of the first signal (the signal being proportional to the detected fluorescence by the at least one of the one or more light receivers) to a predefined threshold for the signal. The near-real time is less than 10 s, preferably less than 5 s, more preferably less than 2 s, even more preferably less than 1 s, still even more preferably less than 0.1 s, most preferably less than 0.05 s. An advantage of an apparatus of the present disclosure for detection of fluorescence of the sample is near-real time feedback to the user of fluorescence of fluorophores comprised in the sample obtained from the object. Another advantage of an apparatus of the present disclosure is detection of otherwise visually undetectable fluorophores, i.e. the fluorophore concentrations being too low for visual detection (a clinically relevant amount of the fluorophore being too low for visual detection) or the wavelength(s) of the fluorescence of the fluorophores being at a wavelength not detectable by human eyes. In particular, an apparatus of the present disclosure enables guidance to a surgeon, during FGS, to remove less vital or important tissue of the object (human or animal), since after the surgical cavity of the object has been emitted with light that excites fluorophores (e.g. blue light when exciting PpIX), in order to visually detect parts to be removed in the surgical cavity due to the fluorescence of the generated fluorescence, the surgeon may switch the wavelength of the light source to white light and remove a sample comprising one or more fluorophores and representing a disease or condition. In the case the surgeon removes a sample generating fluorescence less than a predefined threshold value of fluorescence (e.g. tissue not representing a disease or condition), the surgeon is given feedback by the apparatus via the outputted information. Subsequently, the surgeon may stop removing further samples from the surgical cavity thus saving vital tissue of the patient. Therefore, an apparatus of the present disclosure enables identifying non-fluorescent areas of the surgical cavity to minimize damage to healthy tissue. In addition, an apparatus of the disclosure enables near-real time detection of fluorescence during surgery and fastens up the operative performance of the surgeon.

Furthermore, since the apparatus of the present disclosure emits light that excites one or more fluorophores of the sample being transported away from the object in the transparent conduit, excitation light emitted towards the surgical cavity can be reduced, thus reducing photobleaching of the fluorophores and subsequently increasing the surgery time.

The benefits and technical effects of using detection based on fluorescence in the current invention compared to other detection methods can be summarised as, increased sensitivity, accuracy and speed of detection. Increased sensitivity means that the detection based in fluorescence is highly sensitive and can detect even small amounts of fluorescence in the sample. Increased accuracy again means that the detection is very specific to detect only samples where the specific fluorescence is induced. Fluorescence in form of fluorophores is induced to the sample, such as cancer tissue, before detection. Therefore, it is only the detectable tissue or sample, which is fluorescent, and the detection is therefore very specific to the sample or tissue of interest. The speed of the detection is again of essence since it enables fast reaction due to changes in the detected fluorescence.

More specifically, the accuracy and speed of the detection of the current invention enables analyses of flowing tissues, both laminar and turbulent, and not only aerosols or vapours. The sensitivity of fluorescence enables that targeted fluorophores can be detected from deeper inside a solution. The detection is not affected by the composition of the sample to be analysed (detected) and the apparatus is also suitable for analysing samples such as mixtures of liquids, tissues and aerosols. In addition, all samples, including macroscopic and microscopic, transported in the transparent conduit are analysed and detected for fluorescence, not only some specific samples, such as aerosols.

It is relevant to understand, that fluorescence is not a specular reflection of light, and light is not only a waveform phenome, but a particle. Using fluorescence as opposed to specular reflections or absorbance, and photons as opposed to waveform patterns, enables both higher sensitivity and flexibility of the current invention, when analysing the tissues within the conduit. The higher sensitivity is contributed by the aforementioned insight, that fluorescence is essentially a light source within the conduit, which can be detected from any unobstructed direction—as opposed to reflections or absorbance. Furthermore, the fluorescence causes secondary effects such as heat and vibration, which may be detected with e.g., waveform detectors. It can be declared, that combining the information from photon and waveform detectors can lead to increased sensitivity on specific conditions, and one does not rule out the other. It is relevant to understand, that in this concept, utilization of sensors other than those sensitive to photons at specific wavelengths, such as waveform photoacoustic imaging or Raman spectrometry, can supplement the analysis by detecting the secondary effects referred to as the 'fluorescence interference'—especially heat generation and vibrations. Also, the fluorescence is characterized by its half-time referred to as 'fluorescence decay', which in addition to the fluorescence peak wavelength, can be altered by the mixtures features such as temperature, pH, and subtle tissue components.

An added benefit is, that the components of the mixture can be altered to increase the sensitivity of the detector according to the invention, the alteration can be performed for example by modifying the tissue irrigation liquid. These subtle features associated to fluorescent makes it much more flexible in terms of medical applications than those depending on non-fluorescent light.

In this invention, the differences between fluorescence lifetime can be detected due to the laminar flow-model and sample flow within the conduit, as opposed to a stand-alone probe placed on a tissue. Analysing the samples fluorescent features within the conduit, as opposed to a probe from one angle, allows much higher sensitivity as the amount of light excitation and emission can be achieved higher—up to levels that could be harmful if applied on living tissues. The 360-degrees of freedom for placement of both the light sources and the detectors on any angle around the conduit minimizes lights obstruction, for excitation and emission, to and from the target. In addition, the black box design, enabled by the postresection design, yields better noise-to-signal ratio as opposed to probes utilized on non-resected living tissues, that are contaminated by other light sources.

The invention is based on detection of fluorescence, i.e. fluorescent emission, fluorescent interference or fluorescent decay, originating from a targeted tissue where the specific fluorophores have been induced. This enables very specific and accurate tissue specific detection. In addition, there is no need for "learning the system", since the fluorescence is based on a pre-determined fluorophore, with known fluorescent properties. There is not a need for any data-base or the like for signals or outputs for various tissue. Thereby, the detection is not dependent on the tissue per se, but the pre-determined fluorophore induced to the target tissue. Since the detection is fluorophore specific compared to tissue specific, there are no disturbance from the environment or other tissues than the target tissue. The detection is not disturbed by contaminants, disturbances, or other tissue as they are not specified as monitored characteristics. However, even if the detection does not necessary need "learning" or comparison to a database, since the fluorophore is pre-determined, learning based on a database can further enhance the performance.

The invented apparatus can be integrated to existing surgical apparatus, such as an ultrasonic aspirator or a surgical suction device, without disrupting their conventional use. In addition, the apparatus can be integrated to surgical systems for monitoring in- and outflow of fluorescent probes. Such information can be used for optimizing timing, effectiveness or detection of adverse events related to the fluorescent target molecules, which may represent a disease or a health condition.

The apparatus does not necessarily need any additional extra equipment, such as suction tips or specific forceps, or in vivo probes, substances or solutions etc. for detection. Instead, the apparatus itself is a stand-alone apparatus that complements surgical workflow.

Since the housing of the apparatus of the present disclosure is adapted to surround at least a part of the transparent conduit wherein the sample is being transported away from the object, a drawback of using conventional, separate, bulky or handheld apparatus for detecting fluorescence is overcome, in particular during FGS, since the apparatus may be attached to the conduit. An apparatus of the present disclosure may be located very close to the object from where the sample is obtained, e.g. 1-100 cm from the object, or may locate at a distance further away from the object, e.g. 1-10 m from the object. The distance between the housing of the apparatus and the object is not limited, as long as the sample is being transported in the transparent conduit. Where near-real time detection is required, the distance from the housing to the object is preferably short enough to enable near-real time feedback to the user of the apparatus and the housing does not severely negatively interfere with the users work. Preferably, the housing is surrounding the transparent conduit 0.01-10 m from the object from which the sample is obtained, preferably 0.3-10 m from the object, more preferably 0.3-3 m from the object, even more preferably 0.3-1 m from the object. Therefore, an apparatus of the present disclosure is not restricted to only short distances from the object.

Specifically, the apparatus of the disclosure increases the surgeon's ability to identify cancer tissue in a way that reduces the technical limitations currently affecting FGS, with detection based not only on the human eye, but also on the utilization of spectral analysis, e.g. by comparing detected fluorescence to threshold values or determined values. Studies throughout have shown that computational machine-based classification between healthy and diseased tissue is more sensitive and better than the subjective performance of the human eye. Optic spectral analysis, with a method of the present disclosure, can exceed the physiological limitations of the human eye and recognize visually undetectable wavelengths (such as ultraviolet, near-infrared, infrared) of light, also.

Therefore, an apparatus of the present disclosure for detecting fluorescence of samples, being transported in e.g. surgical suction waste, has the advantage of improving patient care, slowing down and reducing tumor recurrence, and increasing patient safety. An apparatus of the present disclosure enables fluorescence detection of a sample comprising one or more fluorophores and representing a disease or a condition (e.g. a tumor), which is visually undetectable by a human eye. Therefore, reduction in postoperative complications adjacent to damage in eloquent brain areas, and reoperations lead to lower healthcare costs.

The term "fluorescence" as used herein and hereafter refers to the emission of light by an atom, molecule, nanostructure, fluorophore, substance, or a sample that has absorbed light or other electromagnetic radiation. It is to be understood that fluorescence is a form of luminescence. In fluorescence, in many cases, the emitted light has a longer wavelength, and therefore lower energy, than the absorbed radiation. Fluorescence occurs when a molecule, atom, nanostructure, fluorophore, substance, or sample has absorbed light or other electromagnetic radiation and is excited, and subsequently relaxes to a lower energy state through emission of one or more photons. Fluorescent atoms, molecules, nanostructures, substances, and samples are fluorophores. It is to be understood that different fluorescent molecules (fluorophores) and atoms may be excited with different wavelengths of light and fluorescent molecules (fluorophores) and atoms may emit light of different wavelength.

The term "sample" as used herein and hereafter refers to a part or piece obtained from an object. Examples of samples include, but is not limited to, tissue such as connective tissue, muscle tissue, nervous tissue, and epithelial tissue; tumors such as brain tumors such as glioma-type tumors and diffuse cancer types such as carcinomatosis and sarcomatosis; body fluids of intracellular and extracellular fluids such as cerebrospinal fluid, urine, and blood; blood cells, and extracellular vesicles.

The terms "represent a disease or condition" as used herein and hereafter refer to a sample obtained from an object and the object has a disease or a condition, wherein the sample comprising one or more fluorophores is an indication for the disease or the condition. Therefore, it is to be understood that if said sample comprises one or more fluorophores said sample may represent a disease or condition. Examples of diseases and conditions include, but is not limited to, cancers such as glioma, non-functional pituitary adenoma, carcinomatosis, sarcomatosis, benign neoplasm, in situ neoplasm, malignant neoplasm, bacterial infection such as caused by *E. Coli*; viral infection, deoxygenation, leakage of cerebrospinal fluid, contamination of body fluid by a harmful or toxic compound, and accumulation or systemic clearance of drug. It is to be understood that fluorescence may be generated by one or more fluorophores comprised in a sample representing a disease or condition due to e.g. at least one of the one or more fluorophores originating from a drug (e.g. indocyanine green, Gliolan i.e. 5-ALA hydrochloride), prodrug (e.g. a methyl ester of 5-ALA, dipeptide derivatives of 5-ALA), precursor or any suitable compound, which may function as a fluorophore, or autofluorescence of a fluorophore (e.g. NAP(P)H, FAD, flavins, collagen, vitamins such as vitamin $A_1$ and $B_2$, $B_6$, and $B_9$, indolamines), mitochondria, or lysosomes comprised in said sample.

The term "object" as used herein and hereafter refers to a human or animal. Therefore, "a sample obtained from an object" refers to a sample obtained from a human or animal by e.g. surgery or invasive medical treatment.

The term "fluorophore" as used herein and hereafter refers to a fluorescent molecule, atom, nanostructure, fluorophore, or substance that can re-emit light upon light excitation, i.e. fluorescence. A fluorophore may or may not be covalently attached by one or more chemical bonds to a sample. Examples of fluorophores include, but are not limited to, PpIX and salts and derivates thereof, indocyanine green and salts thereof, methylene blue, fluorescein and salts thereof (such as fluorescein sodium); cyanines (such as Cy5.5, Cy7, Cy7.5), T700, T800, BLZ-100, GB119, IRDye800CW conjugate, IRDye700DX conjugate, EC17, LUM015, AVB-620, folate-fluorescein isothiocyanate (FITC), OTL38, gGlu-HMRG, green fluorophore conjugates, fluorescently labelled peptides, fluorophore conjugated antibodies, fluorescent nanoparticles, activatable fluorescent probes, endogenous fluorophores, NAP(P)H, FAD, flavins, collagen, vitamins such as vitamin $A_1$ and $B_2$, $B_6$, and $B_9$; indolamines, mitochondria and lysosomes, and derivatives, isomers and salts thereof, or combinations thereof. It is to be understood that one or more fluorophores comprised in a sample may originate from a drug, prodrug, precursor, or any suitable compound, which may function as a fluorophore, that may be or may not be converted, e.g. in biosynthesis or with a reaction, to a fluorophore. Therefore, said drug, prodrug, precursor or any suitable compound, which may function as a fluorophore, may be converted to different derivatives of the fluorophore. An example of a precursor/drug converted to a fluorophore is the fluorescence inducing photodynamic substance 5-ALA and salts thereof, preferably the hydrochloride salt thereof, which is converted in the human body to fluorescent PpIX and derivatives thereof. A fluorescent marker or tag may also be a fluorophore.

The terms "sample obtained from an object" in combination with the terms "being transported away from the object in a transparent conduit" as used herein and hereafter refers to a sample obtained from a human or animal, e.g. by surgery or an invasive medical treatment method, which may simultaneously with being obtained, or instantaneously or immediately after being obtained, be transported away from said object in a transparent conduit. The term "being transported" as used herein and hereafter refers to the movement of the sample away from the object by e.g. negative pressure using e.g. a suction device such as, but not limited to, an ultrasonic aspirator or a surgical suction device. Gravity may also cause the sample being transported away from the object. Therefore, it is to be understood that an apparatus for detecting fluorescence of a sample disclosed herein and hereafter may detect fluorescence of a sample while being transported away from the object, i.e. a moving sample, in a transparent conduit. The terms "transparent conduit" as used herein and hereafter refers to a conduit, which allows light to pass through the material of the conduit. Examples of conduits include, but is not limited to, a pipe, tube such as a suction tube, surgical suction tube, medical tube, hygienically sensitive tube; catheter, cannula, suction tip. The outer diameter of the conduit is not limited as long as the conduit may be used in surgery to transport the sample away from the object, e.g. the outer diameter of the conduit may be 1 mm (Fr 3)-60 mm (Fr 180), preferably 1 mm (Fr 3)-20 mm (Fr 60), more preferably 1 mm (Fr 3)-16 mm (Fr 48), even more preferably 2 mm (Fr 6)-16 mm (Fr 48), even more preferably the outer diameter of a surgical suction tube or medical tube of 2.67 mm (Fr 8)-16 mm (Fr 48). The inner diameter of the conduit with said outer diameter may be anything that allows the sample to be transported in the conduit and allowing the conduit to be used in methods of medical treatment, e.g. the inner diameter of the conduit may be 0.75 mm-15.75 mm. An example of a sample obtained from an object and being transported away from the object in a transparent conduit is a piece of a tumor removed from a human with an ultrasonic cavitation device (an ultrasonic aspirator) and simultaneously with the removing being moved from the human into a medical tube and further away from the human.

The term "housing" as used herein and hereafter relates to an arrangement comprising one or more light sources and one or more light receivers (detector), arranged in horizontal, vertical or angular position in said housing, and the housing is being adapted to surround at least a part of a transparent conduit, wherein the one or more light sources may be arranged and operable to emit light towards a sample being transported in the transparent conduit and wherein the one or more light receivers may be arranged and operable to detect fluorescence generated by one or more fluorophores comprised in the sample being transported in the transparent conduit. Optionally, the housing comprises, in addition to the one or more light sources and one or more light receivers, an at least partially closed compartment, having a top section, a bottom section, and openings at opposite longitudinal ends of the housing being adapted to surround at least a part of the transparent conduit. The housing may reduce external light from reaching the light receiver and may reduce the light source and light receiver from becoming dirty. In addition, the housing adapted to surround the transparent conduit enables the housing to be detachably fixed to the conduit, thus enabling the user to fix the housing to the conduit and use one's hands for something else, and to remove the housing from the conduit when the apparatus is not used. The housing may further comprise attaching means, such as a nail and clip, a vacuum suction cup, a screw, a hook, a bolt and nut combination, a bracket, lock, tape, snap lock, hinge, seal, one or more magnets and so on, for attaching one or more parts that the housing may be formed of and/or for locking the one or more parts and/or for attachment externally to the conduit. It is to be understood that the term "surround" as used herein and hereafter refers to the housing at least partially surrounding the conduit or fully surrounding the conduit, preferably the housing fully surrounds the conduit, i.e. encloses the whole perimeter of the conduit. The terms "at least a part of the transparent conduit" as used herein and hereafter refers to the housing surrounding a part of the conduit or the whole conduit, i.e. in respect of the longitudinal axis of the conduit. Furthermore, it is to be understood that the housing may be detachably adapted to surround at least a part of the transparent conduit. Moreover, the housing may be adapted to be detachably fixed to the conduit, with e.g. seals at opposite longitudinal ends of the housing or by the housing squeezing against the conduit. In an embodiment, the housing comprises at least one of the top sections, the bottom section, openings, at least one bore, a switch, and so forth. Furthermore, the switch is operable to cause the one or more light sources of the housing to emit light when in operation or in an ON mode. The at least one bore allows access into the housing, such as by a power supply arrangement, operations, data transfer, and the like. In an example, the housing includes a power supply arrangement, arranged via the at least one bore, for supplying power to the housing. The power supply arrangement may supply power using conventional methods, including, but not limited to, solar power, electrical energy, chemical energy, batteries, rechargeable batteries, fuel-based energy, hydropower, and so on. In another example, the housing may include a power supply arrangement, arranged via at least one power receiver, for supplying power to the housing. The power receiver may extract wirelessly power from an electromagnetic field generated by a transmitter device, driven by electric power from a power source, i.e. power is supplied to the housing by means of a wireless power transmission system. It is to be understood that the computing device may be provided in the housing or outside the housing.

The term "light source" as used herein and hereafter refers to device that emits light. The housing may comprise one or more, e.g. one, two, three or four, or more, light sources. Each light source may emit same or different wavelength, or ranges of wavelengths, of light. Specifically, the light source is operable to emit light towards the sample being transported in the transparent conduit. The light source may emit light at a predefined range of wavelengths. Examples of light sources include, but are not limited to, light emitting diode (LED), laser diode, halogen lamp, incandescent lamp, fluorescent lamp, and LED in combination with quantum dots, or combinations thereof. In a preferred embodiment, at least one of the light sources is an LED, but it can be any other suitable light source, i.e. a light source capable of emitting light at a required narrow wavelength region and required intensity, such as a laser diode. In an embodiment, the housing includes a plurality of light sources, preferably LEDs, for example at least two LEDs, electrically coupled with a power supply arrangement arranged within the housing.

The term "light receiver" as used herein and hereafter refers to a light detector that detects light. The one or more light receivers are operable to detect fluorescence generated by one or more fluorophores comprised in the sample being transported in the transparent conduit. Specifically, the light receiver may be operable to detect light at a predefined wavelength or range of wavelengths. Examples of light receivers include, but are not limited to, image sensors, such as charge-coupled device (CCD) sensors (e.g. BT-CCD image sensor, CCD leaner image sensor) and metal-oxide-semiconductor (MOS) sensors (e.g. MOS linear image sensor, complementary MOS (CMOS) sensor); photodiodes such as avalanche photodiode (APD); and phototransistors, or any combination thereof.

The term "computing device" as used herein and hereafter refers to devices, comprising computing means, including, but not limited to, a mobile station (mobile phone), smartphone, personal digital assistant (PDA), handset, device using a wireless modem (alarm or measurement device, etc.), laptop and/or touch screen computer, tablet, game console, notebook, and multimedia device. It should be appreciated that a computing device may also be a nearly exclusive uplink only device, of which an example is a laptop loading data (corresponding to one or more signals received from at least one of the one or more light receivers) to a network. A computing device may also be a device having capability to operate in Internet of Things (IoT) network which is a scenario in which systems are provided with the ability to transfer data over a network without requiring human-to-human or human-to-computer interaction. In addition, or alternatively, a computing device may be a device comprising computing means for carrying out at least some of the described methods as disclosed herein and hereafter. Some example computing means for carrying out the processes may include at least one of the following: data acquisition unit, processor (including dual-core and multiple-core processors), digital signal processor, current-to-voltage converter, analog-to-digital converter, amplifier, opto-isolator, controller, data receiver, data transmitter, encoder, comparator, decoder, memory, RAM, ROM, software, firmware, display, user interface, sound means such as a loud speaker, LED, augmented reality interface, user interface, display circuitry, user interface circuitry, user interface software, display software, circuit, antenna, antenna circuitry, and circuitry. It is to be understood that the computing device may be external to the housing or may be comprised by the housing, preferably in the housing. Furthermore, it is to be understood that the computing means may also comprise or may be operatively connected to outputting means via which information may be outputted to a user. Examples of outputting means include, but are not limited to, display, user interface, sound means such as a loud speaker, LED, augmented reality interface, user interface, display circuitry, user interface circuitry, user interface software, display software, circuit, antenna, antenna circuitry, and circuitry.

The term "information" as used herein and hereafter refers to sound, text, light, change in pressure, and data for a computing means, or combinations thereof. Information is outputted by an outputting means operatively connected to the computing means.

In one preferred embodiment the apparatus is adapted for near-real time detecting fluorescence of a sample obtained from an object, the sample comprising one or more fluorophores and representing a disease or condition, and the sample being transported away from the object in a transparent conduit.

In one preferred embodiment the one or more light sources and the one or more light receivers are in the housing. This makes the apparatus easier to use since one can avoid the use of external light sources and light receivers making the apparatus more complex while in use. In addition, the housing protects the one or more light sources and the one or more receivers from getting dirty.

In one embodiment the computing device further comprises means for measuring a level of the fluorescent light, and wherein the outputting indicates the level of the detected fluorescence.

In one preferred embodiment the computing device is connected, preferably communicably coupled, to the housing. In one preferred embodiment, the computing device is communicably coupled to at least one of the one or more light sources and/or one of the one or more of the light receivers by a wire connection or by a wireless connection. In one specific embodiment the computing device is communicably coupled to the one or more of the light receivers comprised in the housing.

In one embodiment the housing comprises:

- one or more light sources operable to emit light towards the sample being transported in the transparent conduit,
- one or more light receivers operable to detect fluorescence generated by one or more fluorophores comprised in the sample being transported in the transparent conduit, and
- the computing device, being communicably coupled to at least one of the one or more light sources and/or one of the one or more of the light receivers, the computing device comprising computing means for:
  - receiving a first signal from at least one of the one or more light receivers, the first signal being proportional to the detected fluorescence by the at least one of the one or more light receivers;
  - comparing the first signal to a predefined threshold for the first signal; and
  - outputting a first information indicating comparison result.

Therefore, it is to be understood that the computing device is provided in the housing.

In one embodiment, the angle between a longitudinal centre axis of the at least one of the one or more light sources and a longitudinal centre axis of the at least one of the one or more light receivers is selected from 0-180°. In one embodiment, the angle is selected from 15-180°. In one embodiment, the angle is selected from 90-180°, preferably 90°. Different angles enable the one or more light sources and the one or more light receivers to be positioned at different locations in the housing.

In one embodiment the height of the housing is from about 10 mm to about 100 mm and the width of the housing is from about 10 mm to about 150 mm. In one embodiment the height of the housing is from about 50 mm to about 70 mm and the width of the housing is from about 80 mm to about 130 mm. It is to be understood that the dimension of the housing is not limited as long as the housing may be adapted to surround at least a part of the transparent conduit.

In one preferred embodiment the computing device comprises means for outputting, in response to the first signal exceeding or being equal to the predefined threshold, a first information on the first signal; and outputting, in response to the first signal failing to exceed or be equal to the predefined threshold, a second information on the first signal.

In one embodiment the housing is adapted to enclose the whole perimeter of the transparent conduit. This may enable minimum external light (i.e. light from the surrounding, outside the housing) from reaching the one or more light receivers thus improving the detection of fluorescence.

In one embodiment the housing is formed of one or more parts being attached to each other with attaching means.

In one embodiment the housing is formed of two parts being attached to each other with attaching means. In one preferred embodiment the attaching means is/are each independently selected from the group consisting of nail and clip, vacuum suction cup, screw, hook, bolt and nut combination, bracket, lock, tape, snap lock, hinge, seal, and one or more magnets. It is to be understood that the attaching means is/are for attaching the two or more parts that the housing is formed of and/or for at least partially enclose the perimeter of the transparent conduit and/or for attachment externally to the conduit.

In one embodiment, the computing device is connected, preferably communicably coupled, to at least one of the one or more light sources and/or one of the one or more of the light receivers. Preferably, the computing device is communicably coupled to the to at least one of the one or more light sources and/or one of the one or more of the light receivers by a wire connection or by a wireless connection. In one preferred embodiment the computing device is communicably coupled to the one or more of the light receivers comprised in the housing.

In one preferred embodiment, the housing comprises:

- one or more light sources operable to emit light towards the sample being transported in the transparent conduit,
- one or more light receivers operable to detect fluorescence generated by one or more fluorophores comprised in the sample being transported in the transparent conduit, and
- the computing device, being communicably coupled to at least one of the one or more light receivers, the computing device comprising computing means for:
  - receiving a first signal from at least one of the one or more light receivers, the first signal being proportional to the detected fluorescence by the at least one of the one or more light receivers;
  - comparing the first signal to a predefined threshold for the first signal; and
  - outputting a first information indicating comparison result.

Therefore, it is to be understood that the computing device, comprised in the apparatus, is in the housing comprised by the apparatus.

In one embodiment, the housing additionally comprises one or more seals for sealing the housing against the transparent conduit. The seal may also decrease or prevent external light from entering the housing.

In one preferred embodiment, the housing comprises seals at opposite longitudinal ends of the housing for sealing the housing against the transparent conduit. The seals may be adjustable seals adapted for sealing the housing against different sizes of transparent conduits when the housing surrounds the conduit, e.g. conduits with an outer diameter of 1 mm (Fr 3)-20 mm (Fr 60), preferably the outer diameter of a surgical suction tube or medical tube with an outer diameter of 2.67 mm (Fr 8)-16 mm (Fr 48). The housing may comprise e.g. 1, 2, 3, 4, 5, 6, 7, or 8 seals.

In one embodiment the one or more light sources are operable to emit, independently from each other, light of one or more fluorescence excitation curve wavelengths of the one or more fluorophores comprised in the sample. In one preferred embodiment, the one or more light sources are operable to emit, independently from each other, light of the peak wavelength of the fluorescence excitation curve, or a range of wavelengths comprising the peak wavelength of the fluorescence excitation curve, of the one or more fluorophores comprised in the sample. In one preferred embodiment, the one or more light sources are operable to emit, independently from each other, light of one or more wavelengths each independently selected from the group consisting of wavelengths from 350 nm to 430 nm, wavelengths from 600 nm to 700 nm and/or wavelengths from 750 nm to 850 nm. In one preferred embodiment the one or more light sources are operable to emit, independently from each other, light of the peak wavelength(s) of the fluorescence excitation curve of a fluorophore selected from the group consisting of PpIX, indocyanine green, methylene blue, fluorescein, and salts thereof; cyanines, T700, T800, BLZ-100, GB119, IRDye800CW conjugate, IRDye700DX conjugate, EC17, LUM015, AVB-620, folate-fluorescein isothiocyanate (FITC), OTL38, gGlu-HMRG, green fluorophore conjugates, fluorescently labelled peptides, fluorophore conjugated antibodies, fluorescent nanoparticles, activatable fluorescent probes, endogenous fluorophores, fluorescent bacteria, fluorescent virus, NAP(P)H, FAD, flavins, collagen, vitamins such as vitamin $A_1$ and $B_2$, $B_6$, and $B_9$; indolamines, mitochondria and lysosomes, and derivatives, isomers and salts thereof, or combinations thereof, preferably selected from PpIX and derivatives thereof, indocyanine green, methylene blue, fluorescein sodium salt. In one preferred embodiment the one or more light sources are operable to emit, independently from each other, light of about 405 nm and/or about 633 nm wavelengths. The housing may comprise one, two, three, four, or more light sources operable to emit, independently from each other, light of one or more fluorescence excitation curve wavelengths of the one or more fluorophores comprised in the sample.

In one embodiment the one or more light receivers are operable to detect, independently from each other, fluorescence at one or more wavelengths of one or more fluorescence emission curves of the one or more fluorophores comprised in the sample. In a preferred embodiment the one or more light receivers are operable to detect, independently from each other, fluorescence of the peak fluorescence emission wavelength of the one or more fluorophores comprised in the sample. In a preferred embodiment the one or more light receivers are operable to detect, independently from each other, fluorescence of one or more wavelengths each independently selected from the group consisting of wavelengths from 600 nm to 655 nm, wavelengths from 650 nm to 695 nm, wavelengths from 700 nm to 790 nm and/or wavelengths from 790 nm to 840 nm. In one preferred embodiment the one or more light receivers are operable to detect, independently from each other, fluorescence generated from one or more fluorophores selected from the group consisting of PpIX, indocyanine green, methylene blue, fluorescein, and salts thereof; cyanines, T700, T800, BLZ-100, GB119, IRDye800CW conjugate, IRDye700DX conjugate, EC17, LUM015, AVB-620, folate-fluorescein isothiocyanate (FITC), OTL38, gGlu-HMRG, green fluorophore conjugates, fluorescently labelled peptides, fluorophore conjugated antibodies, fluorescent nanoparticles, activatable fluorescent probes, endogenous fluorophores, fluorescent bacteria, fluorescent virus, NAP(P)H, FAD, flavins, collagen, vitamins such as vitamin $A_1$ and $B_2$, $B_6$, and $B_9$; indolamines, mitochondria and lysosomes, and derivatives, isomers and salts thereof, or combinations thereof, preferably selected from PpIX and derivatives thereof, indocyanine green, methylene blue, fluorescein sodium salt. The housing may comprise one, two, three, four, or more light receivers operable to detect, independently from each other, fluorescence at one or more wavelengths of one or more fluorescence emission curves of the one or more fluorophores comprised in the sample. In is to be understood that the fluorescence generated by the one or more fluorophores may vary depending on factors such as pH and temperature of the sample.

In one preferred embodiment, the one or more light sources are operable to emit light of the peak wavelength(s) of the fluorescence excitation curve of PpIX or derivatives thereof, and the one or more light receivers are operable to detect fluorescence generated by PpIX or derivatives thereof. It is to be understood that a sample comprising PpIX may represent cancer and PpIX comprised in the sample may originate from 5-ALA, or a prodrug thereof, or another drug administered, e.g. orally, to the object before obtaining the sample, e.g. 1-24 h before obtaining the sample.

Additionally, or alternatively, each of the one or more light sources further comprise one or more emission light filters and/or each of the light receivers comprise one or more incoming light filters. In a preferred embodiment each of the one or more emission light filters is independently selected based on the light source and the one or more peak wavelengths of the fluorescence excitation curve of the one or more fluorophores, and each of the one or more incoming light filters is independently selected based on the light receiver and the one or more peak fluorescence emission wavelengths of the one or more fluorophores.

The term "light filter" as used herein and hereafter refers to a device that selectively transmits light of different desired wavelengths, implemented e.g. as a glass plane or plastic device in the optical path. The optical properties of light filters are described by their frequency response, which specifies how the magnitude and phase of each frequency component of an incoming light is modified by the filter. Examples of light filters include, but are not limited to, absorptive, dichroic, monochromatic, infrared-passing, infrared cut-off, bandstop, longpass, band-pass, shortpass and ultraviolet filters. It is to be understood that a light filter may be emission and incoming light filters, i.e. emission light filters are used to alter the wavelength and/or intensity of the light emitted by the light source, and incoming light filters are used to alter the wavelength and/or intensity of the light received by the light receiver.

In one embodiment the one or more fluorophores comprised in the sample are each independently selected from the group consisting of PpIX, indocyanine green, methylene blue, fluorescein, and salts thereof; cyanines, T700, T800, BLZ-100, GB119, IRDye800CW conjugate, IRDye700DX conjugate, EC17, LUM015, AVB-620, folate-fluorescein isothiocyanate (FITC), OTL38, gGlu-HMRG, green fluorophore conjugates, fluorescently labelled peptides, fluorophore conjugated antibodies, fluorescent nanoparticles, activatable fluorescent probe, endogenous fluorophore, or combinations thereof.

In one embodiment the at least one of the one or more light sources is located before the one or more light receivers in respect of the transport direction of the sample being transported in the transparent conduit. This arrangement of the at least one of the one or more light sources and the one or more light receivers enables more effective excitation of the one or more fluorophores.

Additionally, or alternatively, the housing comprises at least a first light source and the one or more light receivers comprise at least a first light receiver and a second light receiver, positioned so that a distance from the first light receiver to the first light source is less than the distance from the second light receiver to said first light source, and wherein the computing means is further configured to verify a fluorescence detection of the first light receiver from two or more light receivers by:

- receiving the first signal from the first light receiver, the first signal being proportional to the detected fluorescence by the first light receiver;
- determining, in response to the receiving the first signal, a verifying value for the second signal;

receiving a second signal from the second light receiver, the second signal being proportional to the detected fluorescence by the second light receiver;

comparing the second signal to the verifying value;

outputting, in response to the second signal exceeding or being equal to the verifying value, a first information on the second signal; and outputting, in response to the second signal failing to exceed or be equal to the verifying value, a second information on the second signal.

It is to be understood that different fluorophores may have different fluorescence induction speeds and fluorescence decays. Due to excitation light, fluorescence of a fluorophore may be induced after a certain time, i.e. the fluorescence induction speed. Fluorescence decay refers to the time the fluorophore emits fluorescence after being excited by excitation light. When receiving a first signal a computing means may determine what the value of the second signal should be (verifying value for the second signal), taking into account one or more of the distances between the first light source, the first light receiver and the second light receiver, and the fluorescence induction speed and/or fluorescence decay of the fluorophore. If the second signal received by the second light receiver exceeds or is equal to the verifying value, an outputted first information of the second signal may be different from an outputted second information due to the second signal received by the second light receiver fails to exceed or being equal to the verifying value.

Using at least two light receivers may improve the sensitivity and/or the specificity of the fluorescence detection.

Additionally, or alternatively, the housing comprises at least a first light source and the one or more light receivers comprise at least a first light receiver and a second light receiver, wherein a distance between the at least a first light receiver and a second light receiver is selected from one or more distances based on a fluorescence induction speed, fluorescence decay, and fluorescence intensity, or a combination thereof, of the sample comprising one or more fluorophores.

It is to be understood that locations of the one or more light sources and the light receivers may be positioned at different locations of the housing. Depending on the fluorescence induction speed, fluorescence decay, and fluorescence intensity of the fluorophore comprised in the sample, a distance between a first light receiver and a second light receiver may be chosen. For example, if the fluorescence induction speed is low (short) and/or the fluorescence decay is long, the distance may be bigger than if the induction speed is high (long) and/or the fluorescence decay is short. Furthermore, if the fluorescence intensity is high, the distance may be bigger, since the fluorescence may be detected for a longer time. Additionally, or alternatively, a computing means for calculating a flow speed of the sample being transported in the transparent conduit may be comprised in the computing device. To calculate the flow speed, the distance between a first light receiver to a second light receiver may be divided by the difference in time of a first signal received from a first light receiver and a second signal received from a second light receiver. The calculated flow speed may be used in the calibration of the apparatus.

In one embodiment the housing is surrounding the transparent conduit 0.01-10 m from the object from which the sample is obtained, preferably 0.3-10 m from the object, more preferably 0.3-3 m from the object, even more preferably 0.3-1 m from the object. It is to be understood that the distance between the housing of to the object is not limited, as long as the sample is being transported in the transparent conduit. This enables the apparatus to be used in e.g. surgery. Where near-real time detection is required, the distance from the housing to the object is preferably short enough to enable near-real time feedback to the user of the apparatus and the housing does not severely negatively interfere with the users work. The housing may be detachably adapted to surround at least a part of the transparent conduit. Therefore, an advantage of the apparatus is that it may be removed from the transparent conduit if not used and the distance from the housing to the object may be chosen depending on how much space there is around the object.

In one embodiment the computing device is provided in the housing.

In an embodiment, at least one processor, memory, computer program code and user interface form computing means of the computing device.

In one embodiment, the housing further comprises an ON/OFF switch and means for outputting information such as a user interface, augmented reality interface, sound means, display, LED). Additionally, the housing may further comprise at least one of LED for indicating status of the apparatus, successful calibration, positive detection, and/or battery level and a charging and/or data port.

In an embodiment, the computing device is communicably coupled to at least one of the one or more light receivers, the computing device comprising:

at least one processor; and at least one memory including computer program code, said at least one memory and computer program code configured to, with said at least one processor, cause per-forming:

receiving a first signal from at least one of the one or more light receivers, the first signal being proportional to the detected fluorescence by the at least one of the one or more light receivers;

comparing the first signal to a predefined threshold for the first signal; and outputting a first information indicating comparison result.

In another aspect, an embodiment of the present disclosure provides a method for detecting fluorescence of a sample obtained from an object, the sample comprising one or more fluorophores and representing a disease or condition, and the sample being transported away from the object in a transparent conduit, the method comprising:

i) transporting a sample, comprising one or more fluorophores and representing a disease or condition, in a transparent conduit away from the object;

ii) emitting light towards the sample being transported in the conduit;

iii) detecting fluorescence generated by one or more fluorophores comprised in the sample being transported in the conduit.

In one embodiment the method further comprises:

iv) generating a first signal being proportional to the detected fluorescence;

v) comparing the first signal to a predefined threshold for the first signal; and vi) outputting a first information indicating comparison result.

In one embodiment the method further comprises, before i) or ii), preferably before i), adapting a housing to surround at least a part of the transparent conduit, the housing comprising:

one or more light sources operable to emit light towards the sample being transported in the transparent conduit, one or more light receivers operable to detect fluorescence generated by one or more fluorophores comprised in the sample being transported in the transparent conduit, and optionally a computing device comprising computing means for per-forming steps v) and vi).

Additionally, or alternatively, a method as disclosed in the present disclosure is a method for near-real time detecting fluorescence of the sample.

In one embodiment, the sample is transported away from the object by negative pressure. It is to be understood that negative pressure is a pressure that is less than the surrounding pressure. A negative pressure may be achieved with e.g. an ultrasonic aspirator or a surgical suction device.

In one embodiment the method further comprises a step of emitting light towards the object before the sample is obtained and being transported away from the object in the conduit. Preferably, the light excites one or more fluorophores comprised in the sample.

In one embodiment, the method further comprises a calibration step, wherein the sample is a calibration composition comprising a fluorophore of known fluorescence and concentration. Preferably, the calibration step is before step i).

Additionally, or alternatively, the method further comprises verifying a fluorescence detection, the verifying a fluorescence detection comprises the steps:

detecting a second fluorescence generated by one or more fluorophores comprised in the sample being transported in the conduit;

generating a second signal being proportional to the detected second fluorescence;

determining, in response to the generated first signal, a verifying value for the second signal;

comparing the second signal to the verifying value;

outputting, in response to the second signal exceeding or being equal to the verifying value, a second information on the second signal; and outputting, in response to the second signal failing to exceed or be equal to the verifying value, a third information on the second signal.

Additionally, or alternatively, the method further comprises a step for determination of the flow speed, wherein the sample is a calibration composition comprising a fluorophore of known fluorescence and concentration, the determination of the flow speed comprises the steps:

calculating, in response to generating the first signal and the second signal, a first time value based on the difference in time between generating the first signal and the second signal;

calculating, in response of calculating the first time value, a flow speed value based on dividing a predefined distance value with the first time value; and outputting a fifth information indicating calculation result of the flow speed value.

In one embodiment of the present disclosure is provided a method for detecting fluorescence of a sample obtained from an object, the sample comprising one or more fluorophores and representing a disease or condition, and the sample being transported away from the object in a transparent conduit, the method comprising:

i) removing a sample, preferably a part of a tumor, from an object, preferably from a human, ii) transporting the sample, comprising one or more fluorophores and representing a disease or condition, in a transparent conduit away from the object;

iii) emitting light towards the sample being transported in the conduit;

iv) detecting fluorescence generated by one or more fluorophores comprised in the sample being transported in the conduit;

v) generating a first signal being proportional to the detected fluorescence;

vi) comparing the first signal to a predefined threshold for the first signal; and vii) outputting a first information indicating comparison result.

In another aspect, an embodiment of the present disclosure provides a use of an apparatus as disclosed in the present disclosure in a method selected from the group consisting of an invasive medical treatment method, a detection method of a diseased tissue or a diseased body fluid comprising one or more fluorophores and representing a disease or condition, a detection method of a tumor and in the diagnosis of cancer. Preferably, the diagnosis of cancer is in vitro or ex vivo diagnosis of cancer.

In another aspect, an embodiment of the present disclosure provides a kit-of-parts of an apparatus as disclosed in the present disclosure combined with a transparent conduit. In one embodiment the perimeter of the conduit is such that the housing can enclose the whole perimeter of the conduit. In one embodiment the outer diameter of the conduit is 1 mm (Fr 3)-60 mm (Fr 180), preferably 1 mm (Fr 3)-20 mm (Fr 60), more preferably 1 mm (Fr 3)-16 mm (Fr 48), even more preferably 2 mm (Fr 6)-16 mm (Fr 48), even more preferably the outer diameter of a surgical suction tube or medical tube of 2.67 mm (Fr 8)-16 mm (Fr 48). The inner diameter of the conduit with said outer diameter may be anything that allows the sample to be transported in the conduit and allowing the conduit to be used in methods of medical treatment, e.g. the inner diameter of the conduit may be 0.75 mm-15.75 mm. In one embodiment the kit-of-parts further comprises a leaflet of information of how to use the apparatus.

In another aspect, an embodiment of the present disclosure provides a method of surgery, a method of treatment of a disease or a condition, or an in vivo diagnosis of a disease or a condition using an apparatus as disclosed in the present disclosure. In one embodiment the disease is cancer. In one embodiment the method of surgery comprises surgery of cancer.

In another aspect, an embodiment of the present disclosure provides a method for detecting fluorescence of a sample comprising one or more fluorophores and representing a disease or condition, using an apparatus as disclosed in the present disclosure.

In another aspect, an embodiment of the present disclosure provides an apparatus as disclosed in the present disclosure for carrying out a method as disclosed in the present disclosure.

EXPERIMENTAL SECTION

In an exemplary implementation, experiments were conducted in a microsurgical research and training centre. The experiments describe a method disclosed in the present disclosure for detecting fluorescence of samples. The samples comprise PpIX with concentrations representing active gliomas, wherein the samples can be detected by the fluorescence of PpIX as good or better than persons skilled in the art. Fluorescence of samples, comprising fluorophores, was detected from a surgical resection fluid flowing through a suction tube, i.e. samples being transported away from an object in a transparent conduit.

Homological PpIX samples were prepared according to in vivo PpIX concentration range in grade IV gliomas documented during resection as described in Johansson et al. (Johansson, Ann, et al. "5-Aminolevulinic acid-induced protoporphyrin IX levels in tissue of human malignant brain tumors." Photochemistry and photobiology 86.6 (2010): 1373-1378), the PpIX samples representing the disease or condition. The samples were suctioned (i.e. transported away) with a surgical suction pump system and fluorescence was detected with an apparatus as disclosed herein. Placenta tissue debris and fluid simulating blood were suctioned together with the PpIX samples, also separately in between the PpIX samples, to simulate surgery during resection of active glioma cells and surrounding healthy nervous tissues.

Fluorescent PpIX solutions were prepared in a histochemical laboratory according to Taniguchi et al. (Taniguchi, Hiroki, et al. "Improving convenience and reliability of 5-ALA-induced fluorescent imaging for brain tumor surgery." International Conference on Medical Image Computing and Computer-Assisted Intervention. Springer, Cham, 2015). Normal saline (B. Braun, Melsungen AG, Germany) was heated to +100° C., gelatin (#G2500, Sigma-Aldrich Company, St. Louis, MO, USA) was added and the mixture was allowed to cool to +37° C. PpIX disodium salt (#258385, Sigma-Aldrich, 2.02 mg) was dissolved in dimethyl sulfoxide (DMSO, #D4540, Sigma-Aldrich, 20 ml) to give a PpIX solution. To achieve PpIX samples with predetermined PpIX concentrations, either 1.33 ml of the PpIX solution or DMSO (1.33 ml) was combined with 34.7 ml of the gelatin-saline-mixture prior to mixing with 4.0 ml of Intralipid solution 20% (fat emulsion comprising soya oil (20%, w/v), egg lecithin, glycerol, sodium hydroxide and water; Fresenius Kabi AB, Uppsala, Sweden). The formed gelatinous PpIX samples were solidified and stored at a constant temperature (+4° C.). PpIX samples were prepared according to equation (1), in which D=concentration of PpIX as free acid in the PpIX sample (mol/l), $C \approx 3.0 \times 10^{-6}$ mol/l, k=0 or 2.00:

$$D=kC \quad (1)$$

The PpIX samples were imputed to two concentration groups; the first concentration group comprising three 2C PpIX samples and the second concentration group comprising eight control samples (D=0C) according to visual detection by human (in brackets), as determined by expert surgeons:

1. 0C PpIX (control samples, no PpIX, no fluorescence)
2. 2C PpIX+++(true positive samples; ca. $6.0 \times 10^{-6}$ mol/I PpIX, fluorescence representative of active grade IV glioma cells and visible to expert eye)

3D printed testing platforms containing hexagon shaped slots (diameter 1 cm) and matching lids, to protect the samples from light exposure, were manufactured with Zmorph 2.0 SX-3D printer and from polylactid acid (PLA). The platforms were designed with Autodesk Fusion 360 (v.2.0.6037) and made to ensure that the suction of the samples could be performed swiftly as in glioma surgery. Therefore, the slots represent the object of the present disclosure, from which the sample is obtained.

A surgical suction pump (Medela Dominant Flex) was set at available constant maximum vacuum of −80 kPa equivalent to the flow rate of 50 l/min. Suction handle (Mediplast 6066500400BP) (diameter 4.0 mm, length 80 mm) made from stainless steel, equipped with a round hub, was applied to transparent, sterile, PVC suction tube (CH25, diameter 5.8/8.3 mm, length 3.5 m). The other end of the tube was connected to a 1 litre suction waste container. Identical suction tubes and suction waste containers are used in the operating theatre environment. For the samples to resemble the size and composition of extracted tumor tissue, they were suctioned via the metal suction handle. The apparatus for detecting fluorescence was surrounding the PVC suction tube at the length of ⅓ of the PCV suction tube from the suction handle, i.e. about 1.17 m from the suction handle and about 1.25 m from the tip of the suction handle (i.e. about 1.25 from the object).

Blood simulating fluid was prepared by adding red dye (Dr Oetker Red colouring) to water in a ratio of 1:20 (e.g. 5 ml red dye and 100 ml water). To add noise to the fluorescence detection and to verify the reliability of the method, bits of biological tissue debris was added amongst the PpIX samples prior to suction. The analysis took place in a room designed for surgical and spectral experiments, enabling the elimination of background lighting.

Narrow band LED (M405L2 UV (405 nm), Mounted LED, 1000 mA, 410 mW (Min), Thorlabs) was used as fluorescence excitation light source to emit light towards the sample being transported in the conduit. Hamamatsu PMA-11 spectrometer (Model C7473-36, light receiver, connected to a computer (computing device)) was used to detect fluorescence generated by fluorophore comprised in the sample being transported in the conduit. The light source and light receiver located perpendicularly to the conduit, i.e. the angle between a longitudinal centre axis of the light source and a longitudinal centre axis of the light receiver was about 90°. The excitation light source induced fluorescence of the PpIX samples comprised in the surgical drainage fluid and fluorescence was detected near-real time with the spectrometer. Experiments were performed using excitation and emission narrow band-pass filters. The blue light from the excitation light source was filtered using Semrock 414/46-Brightline single-band filter to eliminate other than the desired excitation light. Semrock 632/22-Brightline single-band filter (incoming light filter) was attached to the spectrometer to filter out background lighting.

The detection and analysis were conducted using the same suction rate (50 l/min) and exposure time (80 ms) of the spectrometer for both the 2C and 0C PpIX samples in three different test-run variations: in slots were placed i) PpIX sample (2C or 0C)+water, ii) PpIX sample (2C or 0C)+blood simulating fluid, or iii) PpIX sample (2C or 0C)+blood simulating fluid+placenta tissue debris. Every second slot was filled with control fluid (water) that was used to clean the detection site and to imitate physiological saline which is also suctioned during glioma surgery. The spectrometer was set to conduct 100 fluorescence detection measurements which, with the exposure time of 80 ms, took 8 seconds. The exposure time corresponds to the amount of time that the detector is exposed to light.

All three test-run variations were performed using the two PpIX sample concentrations (2C and 0C) and without PpIX samples, representing background noise. Before the test-run variations, the 2C and 0C PpIX samples were cut to cube-shaped bits of lengths 2-4 mm. Similarly, pieces of placenta tissue were cut to cube-shaped pieces of lengths 2-4 mm. During the i) first test-runs; three bits of 2C PpIX samples were placed with 1 ml water to three slots, and three bits of 0C PpIX samples were placed with 1 ml water to three slots, i.e. totally six slots comprising three bits of either 2C or 0C PpIX samples in each slot. In the ii) second test-runs; three equally prepared bits as in the first run were placed with 1 ml blood simulating fluid to three slots. For the iii) third test-runs, three equally prepared bits as in the first test-run were placed to three slots together with 1 mL blood simulating fluid and three pieces of placenta tissue per slot, to test whether random suctioned leftover tissue affects the fluorescence detection and spectrometer analysis. This resulted in total 9 bits of both 2C and 0C for each test-run variation analysis.

The background noise was determined using the identical suction rate and exposure time as with the sample measurements and in total three test-run variations were conducted without including PpIX samples. The background noise was recorded as the number of photon counts recorded by spectrometer.

During the fluorescence detection of the PpIX samples, PpIX samples were considered to be detected if fluorescence at 630 nm exceeded a predefined threshold. In the method, the predefined threshold was determined to the average background noise level plus 40% of the background noise level. The average background noise level was equal to 560 photon counts (per 80 ms) and therefore, the predefined threshold was 784 photon counts. The photon counts correspond to the photocurrent (signal) received from the light receiver of the spectrometer by the computing means of the computing device.

For each test-run variation the number of fluorescence signal peaks whose photo count (photocurrent, proportional to the fluorescence detected by the light receiver) exceeded the predefined threshold was counted, corresponding to the number of detected PpIX samples. In addition, the average of the photon counts (of light of 630 nm wavelength) at the signal peaks (i.e. the average of the maximum photocurrents) of each fluorescence signal peak whose photo count exceeded the predefined threshold was calculated. Therefore, the signal proportional to the detected fluorescence was generated and compared to the predefined threshold. Table 1 illustrates the averaged fluorescence intensity values and the number of detected fluorescence intensity peaks for each conducted test-run variation.

TABLE 1

Summary of measurement results.

| Sample group | Test-run variations [1] | Number of detected peaks [2] | Averaged photon count per peak [3] |
|---|---|---|---|
| 2C | 1) water | 6 | 1992 |
| | 2) blood simulating fluid | 7 | 2864 |
| | 3) blood simulating fluid + placenta | 5 | 2450 |
| 0C | 4) water | 0 | — |
| | 5) blood simulating fluid | 1 | 812 |
| | 6) blood simulating fluid + placenta | 0 | — |

[1] Test-run variations 1-3 comprised each nine 2C PpIX samples and test-run variations 4-6 comprised each nine 0C PpIX samples (2C ≈ 6.0 μM, 0C = no PpIX), placenta = placenta tissue debris.

[2] The number of fluorescence signal peaks whose photo count exceeded the predefined threshold.

[3] The calculated averaged photon count at the signal peaks of each fluorescence signal peak whose photo count exceeded the predefined threshold (at 630 nm) with exposure time of 80 ms. Predefined threshold for positive detected peaks was set at 784 photon counts (background noise × 1.4).

The experiments demonstrated that fluorescence of 2C PpIX samples, the samples simulating grade IV glioma cells, was reliably detected as the observed photon counts (fluorescence) exceeded the photo counts of the control samples and the predefined threshold 3-4 times i.e. information indicating comparison result was outputted. Fluorescence and the 2C samples were detected even when blood simulating fluid (red dye+water) and/or other biological samples (placenta tissue debris), representing random surgical suction debris, was present. In total 18 out of the 27 2C PpIX samples were detected separately and 9 were not; therefore at least 66% of the maximum number of 2C PpIX samples were detected in overall. Some of the non-detected 2C PpIX samples may have been detected among the detected ones, since the samples were of various size (2-4 mm) and the light detector may have detected fluorescence of several samples at the same time. One false positive count for the 0C was detected, however, the photo count exceeded the predefined threshold level only by 28 photon counts. As the photon count of all of the detected 2C PpIX samples were significantly higher than the photon count of the 0C samples and the background noise, the false positive count could be safely excluded by increasing the predefined threshold to e.g. 813 photon counts.

Near-real time detection of fluorophore comprised in the sample being transported in the transparent conduit was achieved in circa 0.04 seconds and calculated according to equation (2), in which Q=flow rate ($m^3/s$), $V_1$=suction handle volume ($m^3$), $V_2$=cylinder volume (m3), $A_1$=suction handle area ($m^2$), $A_2$=cylinder area ($m^2$), $d_1$=suction handle length (m), $d_2$=cylinder length (m), $r_1$=suction handle radius (m) and $r_2$=cylinder radius (m):

$$Q = \frac{V_1 + V_2}{t} = \frac{A_1 d_1 + A_2 d_2}{t} = \frac{\pi r_1^2 d_1 + \pi r_2^2 d_2}{t} \Leftrightarrow t = \frac{\pi\left(r_1^2 d_1 + r_2^2 d_2\right)}{Q} \quad (2)$$

$$t = \frac{\pi \cdot \left(\left(\frac{4.0 \cdot 10^{-3}\ \text{m}}{2}\right)^2 \cdot 80 \cdot 10^{-3}\ \text{m} + \left(\frac{5.8 \cdot 10^{-3}\ \text{m}}{2}\right)^2 \cdot \frac{1}{3} \cdot 3.5\ \text{m}\right)}{50 \frac{10^{-3}\ \text{m}^3}{60\ \text{s}}} = 0.0381972\ \text{s} \approx 38.2\ \text{ms}$$

The viability of a method disclosed in the present disclosure was demonstrated successfully; fluorescence at one or more wavelengths of one or more fluorescence emission curves of the one or more fluorophores comprised in a sample were detected according to the method, wherein the sample was comprised in a fast-flowing fluid being transported in a transparent conduit, in a novel manner that has not been previously described. The results of the fluorescence detection method was outputted with information that e.g. indicated if photon counts (photocurrent being proportional to the detected fluorescence) exceeded, were equal or failed to exceed or be equal compared to a predefined threshold, in near real-time. The results demonstrated that a method of the present disclosure can be used in clinical practice. In respect to the sensitivity to detect clinically relevant concentrations of PpIX; the method also enabled outputting information of the exact fluorescence intensity (photon counts of signal peaks) which an expert is not capable of.

DETAILED DESCRIPTION OF THE DRAWINGS

FIG. 1 shows a block diagram of an apparatus 100 for detecting fluorescence of a sample obtained from an object, the sample comprising one or more fluorophores and representing a disease or condition, and the sample being transported away from the object in a transparent conduit, in accordance with an embodiment of the present disclosure. The apparatus 100 comprises a housing 101, a computing device 180, one or more light sources 110 and one or more light receivers 120. The computing device 180 may be connected to at least one of the one or more light receivers comprised in the housing 101. The connection may be realized by a wire connection or by a wireless connection. In one embodiment, the computing device 180 may be connected to the housing 101. The computing device 180 may be provided in the housing 101 or outside the housing 101.

Figure 2:
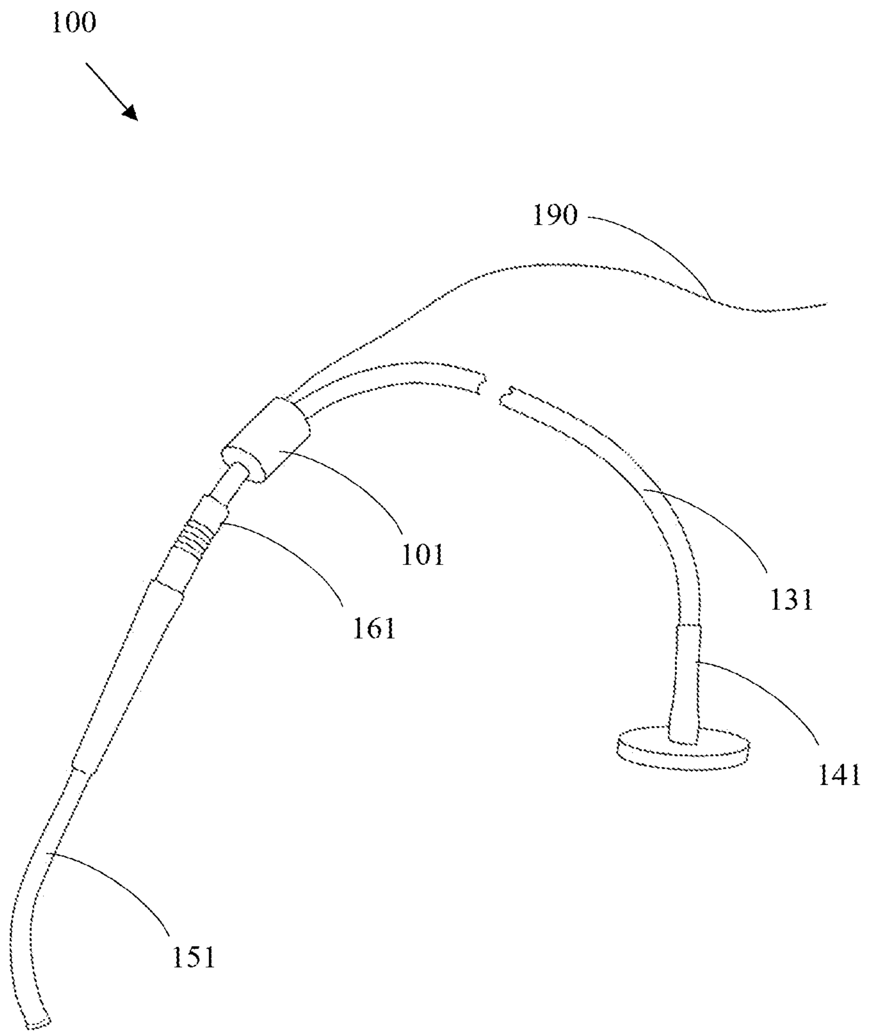
FIGS. 2, 3, 4, and 5 are examples of apparatuses, in accordance with embodiments of the present disclosure.

FIG. 2 shows an embodiment of an apparatus 100 for detecting fluorescence of a sample obtained from an object, the sample comprising one or more fluorophores and representing a disease or condition, and the sample being transported away from the object in a transparent conduit, in accordance with an embodiment of the present disclosure. The apparatus 100 comprises a housing 101 comprising one or more light sources (not shown) and one or more light receivers (not shown), and a computing device (the computing device is not shown). The housing 101 may be adapted to surround at least a part of a transparent conduit 131, or the housing 101 may be adapted to surround fully the transparent conduit 131. The housing 101 may enclose a part or the whole perimeter of a transparent conduit 131, which may be attached to a suction unit attaching means 141 for a suction unit, and the transparent conduit 131 may be attached a tube connector 161, which may be attached to a suction tip 151. The suction unit may be operable to produce a negative pressure for removing and/or transporting the sample from an object (the suction unit and object are not shown). The one or more light sources and the one or more light receivers comprised in the housing 101 are not shown. The computing device (not shown) may be connected to at least one of the one or more light receivers comprised in the housing 101. The connection may be realized by a wire connection 190 or by a wireless connection.

Figure 3:
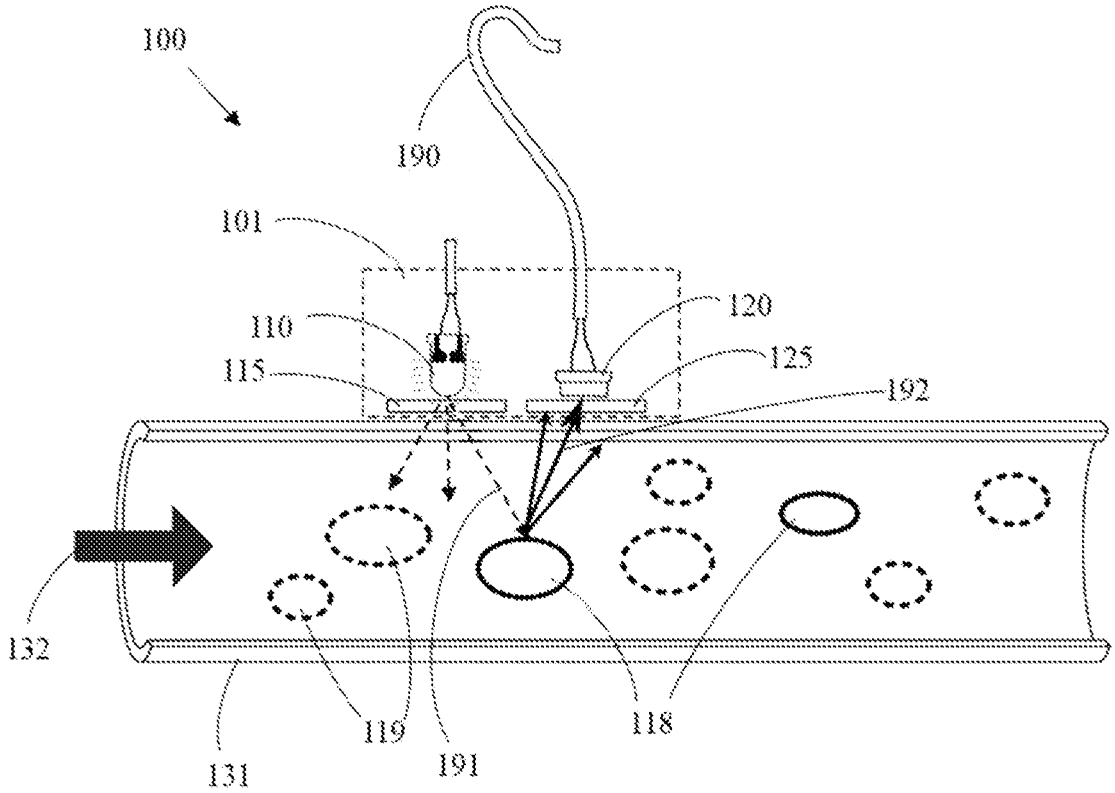

FIG. 3 shows an embodiment of an apparatus 100 for detecting fluorescence of a sample obtained from an object, the sample comprising one or more fluorophores and representing a disease or condition, and the sample being transported away from the object in a transparent conduit, in accordance with an embodiment of the present disclosure. The apparatus 100 comprises a housing 101 and a computing device (the computing device is not shown). The housing 101 may comprise one or more light sources 110 and one or more light receivers 120. The computing device (not shown) may be connected to the housing 101. The connection may be realized by a wire connection 190 or by a wireless connection to at least one of the one or more light receivers 120. The computing device 180 may be provided in the housing 101 or outside the housing 101. The figure shows a cross-section of a transparent conduit 131. The housing 101 may be adapted to surround at least a part of the conduit 131. The housing 101 may enclose the whole perimeter of the transparent conduit 131. Light 191 may be emitted by the light source 110 towards samples 118, 119 obtained from an object and being transported away from the object (not shown). Samples 118 may comprise one or more fluorophores and representing a disease or condition. Samples 119 may not be fluorescent or may not comprise one or more fluorophores. An emission light filter 115 may be used in connection with the light source 110 in order to filter the emitted light. The wavelength(s) of the emitted light by the one or more light sources and the wavelength(s) of the filtered light by the emission light filter 115 may be different. The emitted light and the filtered light by the emission light filter 115 are indicated in FIG. 3 with the dashed arrow 191. The one or more light sources 110 may be operable to emit light 191 towards the conduit 131 and the samples 118, 119 in the conduit 131 while the samples 118, 119 are being transported in the conduit 131. Excited fluorophores comprised in a sample 118 may emit fluorescence 192. The fluorescence 192 may be detected by the light receiver 120. The wavelength(s) of the emitted light 191 and the fluorescence 192 may be different. An incoming light filter 125 may be used in connection with the light receiver 120 in order to filter wavelengths of the emitted fluorescence 192. The wavelength(s) of the emitted fluorescence by the sample 118 and the wavelength(s) of the filtered fluorescence by the incoming light filter 125 may be different. The fluorescence and the filtered fluorescence are indicated in FIG. 3 with the arrow 192. The direction of the transportation (i.e. the flow direction) of the samples 118 and 119 from the object (not shown) in the transparent conduit 131 is indicated by a bold arrow 132. As shown in FIG. 3, at least one of the one or more light sources 110 may be located before the one or more light receivers 120 in respect of the transport direction of the sample being transported in the transparent conduit 131.

Figure 4:
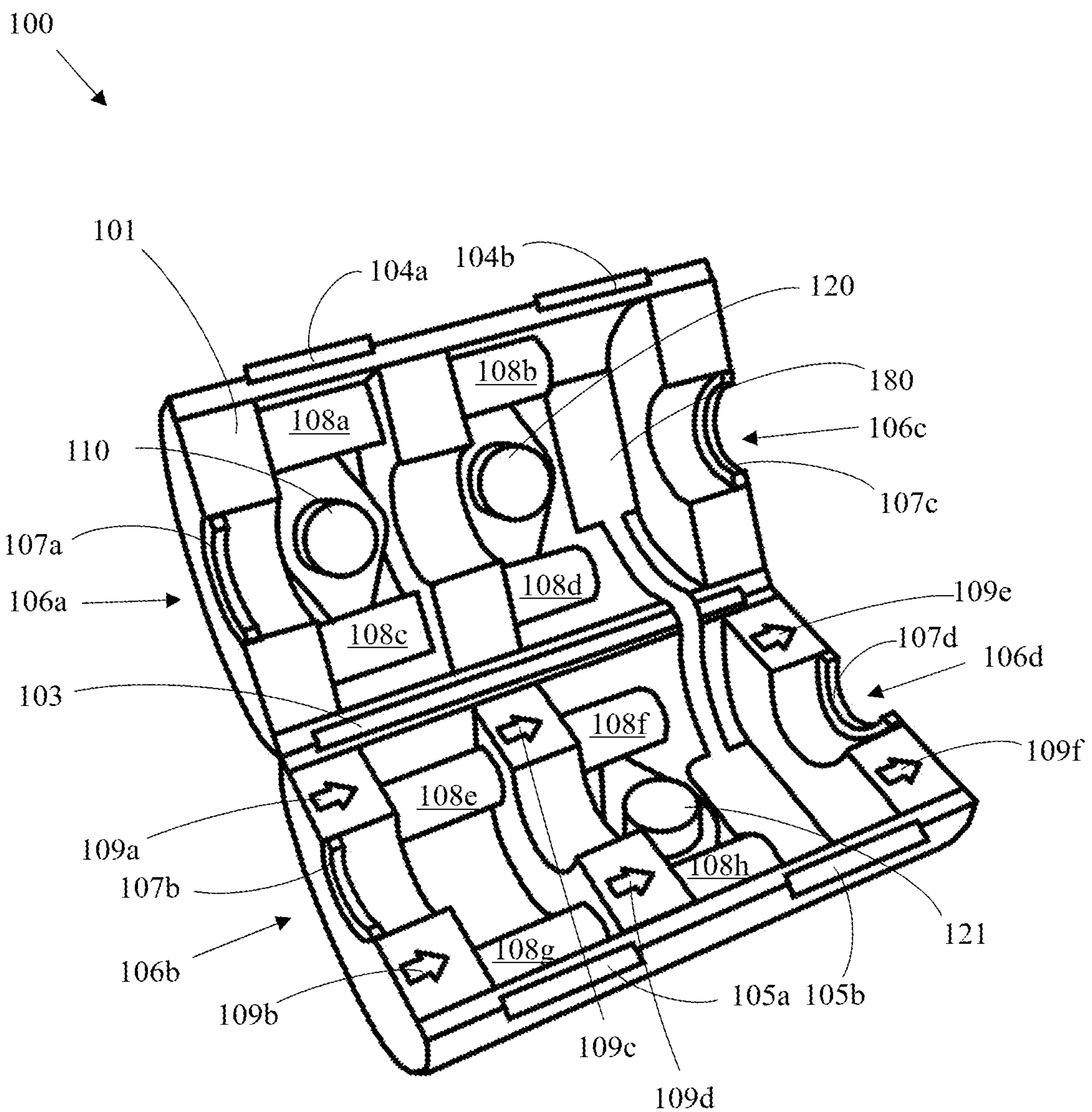

FIG. 4 shows an embodiment of an apparatus 100 for detecting fluorescence of a sample obtained from an object, the sample comprising one or more fluorophores and representing a disease or condition, and the sample being transported away from the object in a transparent conduit, in accordance with an embodiment of the present disclosure. The apparatus 100 comprises a housing 101 and a computing device 180, wherein the computing device 180 may be provided in the housing 101 or outside the housing 101. The housing 101 further comprises one or more light sources 110 and one or more light receivers 120, 121 in the housing 101. The computing device 180 may be communicably coupled to at least one of the one or more of the light receivers 120, 121 and/or to at least one of the one or more light sources 110. The coupling may be realized by a wire connection or by a wireless connection (not shown). The one or more light sources 110 may further comprise an emission light filter 115 and each of the one or more light receivers 120, 121 may further comprise an incoming light filter 125. The housing 101 may be formed of one or more parts. The housing 101 may comprise attaching means 103, **104*a*, 104*b*, 105*a*, 105*b* for attaching the one or more parts that the housing 101 may be formed of (e.g. with a hinge as attaching means 103) and/or for locking the one or more parts (e.g. with magnets as attaching means 104*a*, 104*b*, 105*a*, 105*b*) and/or for attachment externally to the conduit (not shown). It is to be understood that the housing 101 may be detachably adapted to surround at least a part of the transparent conduit and may enclose the whole perimeter of the transparent conduit (not shown). Therefore, the housing 101 may be in an "open position", in a "closed position", or in a position between the "opened position" and the "closet position". In a "closed position", the housing 101 may enclose the whole perimeter of the transparent conduit and the attaching means 104*a*, 104*b*, 105*a*, 105*b* may be arranged to lock the one or more parts to a "closed position". Further, the housing 101 may comprise openings 106*a-d* at opposite longitudinal ends of the housing. The housing 101 may comprise one or more seals 107*a-d* for sealing the housing 101 against the transparent conduit (not shown). The seals may be adjustable seals. Further, the housing 101 may comprise a power supply arrangement 108. The power supply arrangement may comprise one or more components 108*a-h* and each component 108*a-h* may be the same or different and connected (electrically coupled) to the one or more light sources 110, the one or more light receivers 120, 121 and/or the computing device 180 (connection not shown). Furthermore, the housing 101 may comprise one or more indication marks 109***a-f* for indicating an installation orientation of the housing 101 around the conduit. The one or more indication marks 109*a-f* may show the transport direction of the sample being transported away from the object in the conduit (sample, object, and conduit are not shown). At least one of the one or more light sources 110 may be located before the one or more light receivers 120, 121 in respect of the transport direction of the sample being transported in the transparent conduit.

Figure 5:
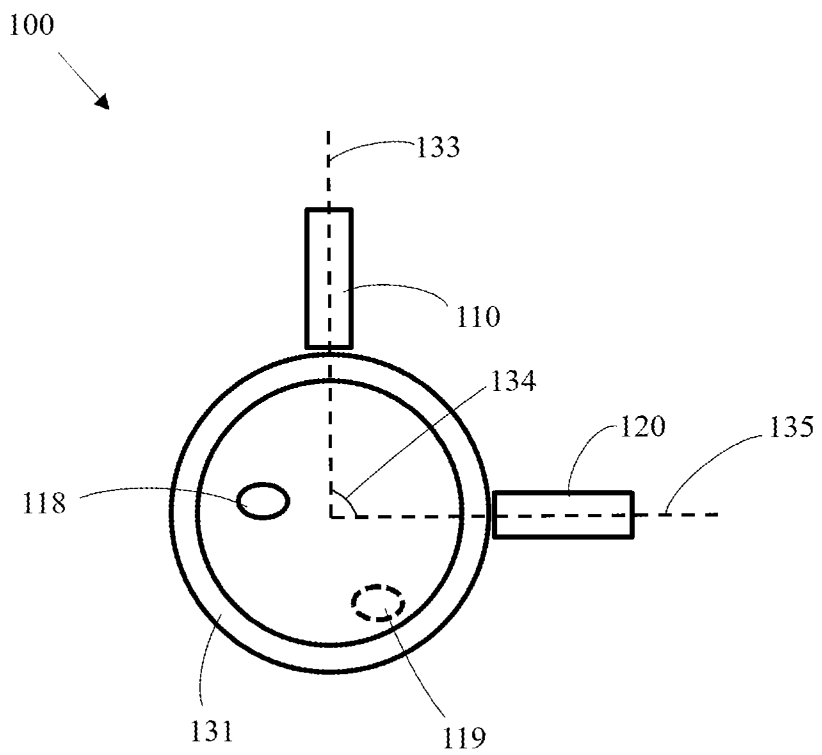

FIG. 5 shows an embodiment of an apparatus 100 for detecting fluorescence of a sample obtained from an object, the sample comprising one or more fluorophores and representing a disease or condition, and the sample being transported away from the object in a transparent conduit, in accordance with an embodiment of the present disclosure. The apparatus 100 comprises a computing device (not shown) and a housing (not shown), which may be adapted to surround at least a part of the transparent conduit 131. The housing comprises one or more light sources 110 and one or more light receivers 120. The computing device (not shown) may be communicably coupled to at least one of the one or more of the light receivers 120. A sample 118 comprising one or more fluorophores and representing a disease or condition and a sample 119 not being fluorescent, or not comprising one or more fluorophores, are shown. Furthermore, the figure shows a cross-section of a transparent conduit 131, which the housing 101 is being adapted to surround at least a part of. An angle 134 between a longitudinal centre axis 133 of the at least one of the one or more light sources 110 and a longitudinal centre axis 135 of the at least one of the one or more light receivers 120, may be in the range of 0-180°. In one embodiment, the angle 134 may be in the range of 15-180°. In one embodiment, the angle may be in the range of 90-180°, preferably 90°.

Figure 6:
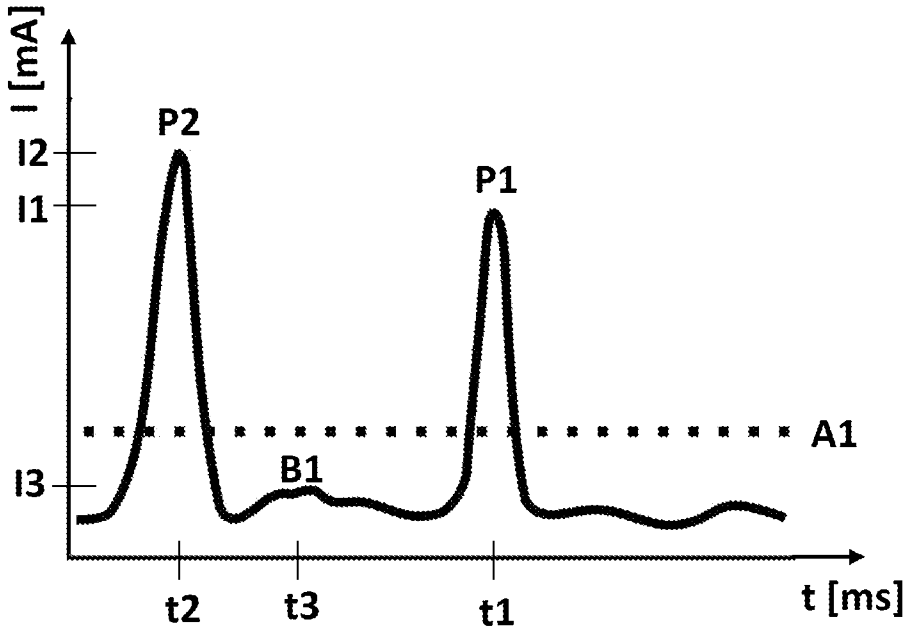
FIG. 6 is an example of the photocurrent I (mA) (indicated with a black line) as a function of time t (ms) received by a computing device from at least one light receiver, with a predefined threshold indicated with a dotted line, in accordance with an embodiment of the present disclosure.

FIG. 6 shows an example of the photocurrent I (mA) (corresponding to one or more signals, indicated with a black line) as a function of time t (ms) received by a computing device 180 from at least one of one or more light receivers 120. A predefined threshold A1 of the photocurrent (signal) is indicated with a dotted line. Fluorescence 192 generated by a one or more fluorophores comprised in a sample 118 may be detected by one or more light receivers 120. The computing device 180, which may be communicably coupled to the at least one light receiver 120, may receive a signal from the light receiver 120. The signal may correspond to the photocurrent I and may be proportional to the detected fluorescence by the at least one light receiver 120. The computing device 180 may compare the signal (photocurrent) to the predefined threshold A1 for the signal (photocurrent). Also shown are two signal peaks P1 (with photocurrent I1 at time t1) and P2 (with photocurrent I2 at time t2) corresponding to maximum photocurrents. The two signal peaks P1,P2 may be proportional to the maximum fluorescence generated by one or more fluorophores comprised in two samples 118*a* and 118*b* detected by at least one of the one or more light receivers 120, wherein the samples 118*a-b* were obtained from an object and transported away from the object in a transparent conduit 131. The two fluorescent samples 118*a-b* passed by the at least one of the one or more light receivers 120 at two different points in time (t1 and t2). P1 may correspond to the maximum fluorescence generated by the first sample 118*a*, which passed by the at least one of the one or more light receivers 120 at time t1 and P2 may correspond to the maximum fluorescence generated by the second sample 118*b*, which passed by the at least one of the one or more light receivers 120 at time t2. Both signal peaks (photocurrents) P1 and P2 may exceed the predefined threshold A1. The figure also shows a photocurrent (signal) B1 (with photocurrent I3 at time t3) received by the computing device 180 from the at least one of the one or more light receivers 120. The photocurrent (signal) B1 may be proportional to a detected fluorescence generated by one or more fluorophores comprised in a third sample 118*c* by the at least one of the one or more light receivers 120. B1 may fail to exceed or be equal to the predefined threshold A1. The computing device 180 may output information indicating comparison result of e.g. the signals (photocurrents) P1, P2 and/or B1.

Figure 7:
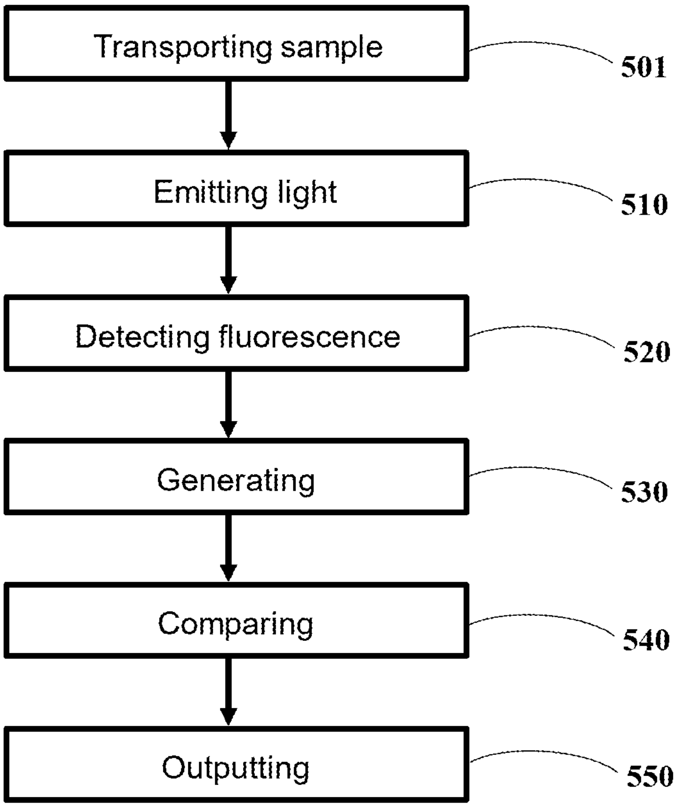
FIG. 7 illustrates a method for detecting fluorescence of a sample, in accordance with an embodiment of the present disclosure.

FIG. 7 shows an embodiment of a method for detecting fluorescence of a sample obtained from an object, the sample comprising one or more fluorophores and representing a disease or condition, and the sample being transported away from the object in a transparent conduit. The method illustrated in the Figure may be carried out by an apparatus comprising a housing being adapted to surround at least a part of a transparent conduit, and a computing device, in accordance with an embodiment of the present disclosure. The sample comprising one or more fluorophores and representing a disease or condition may be obtained from an object. The sample comprising one or more fluorophores is being transported in block 501 away from the object in a transparent conduit. Specifically, the transportation may be achieved by negative pressure using a surgical suction device, an ultrasonic aspirator, or the like. The same suction device, an ultrasonic aspirator, or the like, or a different device may be used to remove the sample from the object. In block 510, the sample being transported away from the object in the transparent conduit may be emitted by light by one or more light sources. In block 520, fluorescence generated by one or more fluorophores comprised in the sample being transported in the conduit may be detected by one or more light receivers. In block 530, a first signal, corresponding to a photocurrent I (mA) and being proportional to the detected fluorescence, may be generated. The generated first signal may be received by a computing means, comprised in a computing device, which may be connected to the fluorescence assembly, from at least one of the one or more light receivers. The generated first signal in block 530 may be compared in block 540 to a predefined threshold for the first signal. In block 550, a first information indicating the comparison result may be outputted. The outputting of the first information may be performed via a user interface of the computing device, such as via a sound means, a display, a LED, haptic feedback such as tremble, or combinations thereof. The first information may be outputted as one or more detection sounds, comprising different volumes, tones, and/or durations, or combinations thereof, or as one or more detection lights, comprising different colours, brightness's, and/or durations, or combinations thereof, or as a combination of one or more detection sounds and one or more detection lights. If the comparison result of the comparison in block 540 is that the first signal exceeds or is equal to the predefined threshold, the outputted first information in block 550 may be different from the outputted information if the comparison result of the comparison in block 540 is that the first signal fails to exceed or be equal to the predefined threshold.

Additionally, or alternatively, block 540 may comprise a first and a second predefined threshold for the first signal. If the comparison result of the comparison in block 540 is that the first signal both exceeds the first predefined threshold and exceeds or is equal to the second predefined threshold, the outputted information in block 550 may be different from the outputted information in block 550 if the comparison result of the comparison in block 540 is that the first signal fails to exceed or be equal to at least one of the first and second predefined threshold.

Modifications to embodiments of the present disclosure described in the foregoing are possible without departing from the scope of the present disclosure as defined by the accompanying claims. Expressions such as "including", "comprising", "incorporating", "have", "is" used to describe and claim the present disclosure are intended to be construed in a non-exclusive manner, namely allowing for items, components or elements not explicitly described also to be present. Reference to the singular is also to be construed to relate to the plural.

The invention claimed is:

1. An apparatus for near-real time detection of fluorescence of a sample obtained from diseased tissue of a human or animal by surgery during fluorescence-guided surgery, the sample including one or more fluorophores, the fluorescence being generated by the one or more fluorophores and being indicative of a disease or health condition, the sample being transported away from the human or animal in a transparent conduit configured to transport the sample as a continuous flow directly from the human or animal to the apparatus for near-real time detection of the fluorescence of the sample, the apparatus comprising:

a housing being configured to surround at least a part of the transparent conduit, the housing comprising:

one or more light sources operable configured to emit light towards the sample being transported in the transparent conduit, the one or more light sources including at least a first light source, and at least two light receivers configured to detect the fluorescence generated by the one or more fluorophores comprised in the sample transported in the transparent conduit, the at least two light receivers comprising at least a first light receiver and a second light receiver, at least the first light receiver and the second light receiver being disposed at a distance based upon one or more of a fluorescence induction speed, fluorescence decay, and fluorescence intensity of the sample comprising the one or more fluorophores;

a computing device configured to:

receive a first signal from at least one of the at least two light receivers, the first signal being proportional to the detected fluorescence by the at least one of the at least two light receivers, compare the first signal to a predefined threshold for the first signal, and output a first information indicating a comparison result.

2. The apparatus according to claim 1, wherein the housing is configured to enclose the whole perimeter of the transparent conduit.

3. The apparatus according to claim 1, wherein the housing is formed of two parts attached to each other with an attachment system.

4. The apparatus according to claim 1, wherein the housing comprises seals at opposite longitudinal ends of the housing to seal the housing against the transparent conduit.

5. The apparatus according to claim 1, wherein the one or more fluorophores comprise at least two fluorophores, the one or more light sources comprise second light source, the first and second light sources being configured to emit, independently from each other, light of eat least two respective fluorescence excitation curve wavelengths of the respective at least two fluorophores comprised in the sample.

6. The apparatus according to claim 1, wherein the at least two light receivers are configured to detect, independently from each other, fluorescence at one or more wavelengths of one or more fluorescence emission curves of the one or more fluorophores comprised in the sample.

7. The apparatus according to claim 1, wherein each of the one or more light sources comprises one or more emission light filters.

8. The apparatus according to claim 1, wherein the one or more fluorophores comprised in the sample are each independently selected from the group consisting of PpIX, indocyanine green, methylene blue, fluorescein, and salts thereof; cyanines, T700, T800, BLZ-100, GB119, IRDye800CW conjugate, IRDye700DX conjugate, EC17, LUM015, AVB-620, folate-fluorescein isothiocyanate (FITC), OTL38, gGlu-HMRG, green fluorophore conjugates, fluorescently labelled peptides, fluorophore con jugated antibodies, fluorescent nanoparticles, activatable fluorescent probe, endogenous fluorophore, and combinations thereof.

9. The apparatus according to claim 1, wherein at least one of the one or more light sources is located before the at least two light receivers in respect of the transport direction of the sample transported in the transparent conduit.

10. The apparatus according to claim 1, wherein the computing device is further configured to verify a fluorescence detection of the first light receiver from the at least two light receivers by:

receiving the first signal from the first light receiver, the first signal being proportional to the detected fluorescence by the first light receiver, determining, in response to receiving the first signal, a verifying value for a second signal, receiving the second signal from the second light receiver, the second signal being proportional to the detected fluorescence by the second light receiver, comparing the second signal to the verifying value, outputting, in response to the second signal exceeding or being equal to the verifying value, a first information on the second signal, and outputting, in response to the second signal failing to exceed or being equal to the verifying value, a second information on the second signal.

11. The apparatus according to claim 1, wherein the computing device is provided in the housing.

12. A method for detecting fluorescence of a sample obtained from diseased tissue of a human or animal by surgery during fluorescence guided surgery, the sample including one or more fluorophores, fluorescence generated by the one Ot more fluorophores being indicative of a disease or health condition, the sample being transported away from the human or animal in a transparent conduit, the method comprising:

transporting a sample, comprising the one or more fluorophores, in the transparent conduit away from the human or animal as continuous flow directly from the human or animal to a detection apparatus configured to detect the fluorescence of the sample;

emitting light, by at least one light source of the detection apparatus, towards the sample being transported in the conduit; and detecting, by at least two light receivers of the detection apparatus, the fluorescence generated by the one or more fluorophores comprised in the sample transported in the conduit, the at least two light receivers comprising at least a first light receiver and a second light receiver, at least the first light receiver and the second light receiver being disposed at a distance selected from one or more distances based on one or more of a fluorescence induction speed, fluorescence decay, and fluorescence intensity of the sample comprising the one or more fluorophores.

13. The method according to claim 12, further comprising:

generating a first signal that is proportional to the detected fluorescence;

comparing the generated first signal to a predefined threshold for the first signal; and outputting a first information indicating comparison result.

14. A kit-of-parts comprising:

the apparatus for detecting the fluorescence of the sample obtained from diseased tissue of a human or animal by surgery during fluorescence guided surgery according to claim 1;

the transparent conduit.

15. The apparatus according to claim 1, wherein each of the at least two light receivers comprises one or more incoming light filters.

16. The apparatus according to claim 1, wherein each of the one or more light sources comprises one or more emission light filters and each of the at least two light receivers comprise one or more incoming light filters.

* * * * *